US005904822A

United States Patent [19]
Casavant

[11] Patent Number: 5,904,822
[45] Date of Patent: May 18, 1999

[54] METHODS AND APPARATUS FOR ANALYZING ELECTROPHORESIS GELS

[75] Inventor: Thomas L. Casavant, Iowa City, Iowa

[73] Assignee: The University of Iowa Research Foundation, Iowa City, Iowa

[21] Appl. No.: 08/748,589

[22] Filed: Nov. 13, 1996

[51] Int. Cl.$^6$ .................................................. G01N 27/26
[52] U.S. Cl. ......................... 204/461; 204/612; 382/129
[58] Field of Search ................................... 204/461, 606; 7/456, 612; 702/22, 23, 25; 382/128, 129

[56] References Cited

U.S. PATENT DOCUMENTS 5,073,963  12/1991  Sammons et al. ....................... 382/128
5,400,249   3/1995  Soll et al. ............................... 382/219

OTHER PUBLICATIONS

CAPLUS abstract of John Lenard ("Protein and glycolipid components of human erythrocyte membranes", Biochemistry (1970), 9(5), 1192–32), 1970 Month Unavailable.
CAPLUS abstract of McKenzie et al. ("Zone electrophoresis of .beta.-lactoglobulins", Nature(London), 1966, 212(5058), 161–3), 1966 Month Unavailable.
CAPLUS abstract of Metzker et al. (Accurate determination of DNA in agarose gels using the novel algorithm GelScann(1.0), Comput. Appl. Biosci. (1995), 11(2), 17–94), 1995 Month Unavailable.
CAPLUS abstract of Bala et al. ("2–DG induced modulation of chromosomal DNA profile, cell survival, mutagenesis and gene conversion in X–irradiated yeast", Indian J. Exp. Biol. (1996), 34(1), 18–26), Jan. 1996.
Sanders et al. ("Imaging as a tool for improving length and accuracy of sequence analysis in automated fluroescence-–based DNA sequencing", Electrophoresis, 1991, 12, 3–11), 1991 Month Unavailable.

*Primary Examiner*—William H. Beisner
*Assistant Examiner*—Alex Noguerola
*Attorney, Agent, or Firm*—Fleshner & Kim

[57] ABSTRACT

This invention relates to a system and methods for the straightening an electrophoresis gel image in the vertical and horizontal directions, and for analyzing a straightened gel image. The system includes an input unit for receiving raw data from the electrophoresis gel, a straightening unit for providing a straightened gel image, an output unit for portraying the raw data from the electrophoresis gel and the straightened gel image, and a an analyzing unit for analyzing the data portrayed in the straightened gel image. The system features a dye boost feature for boosting the intensity of bands, filtering means for modifying the gel image, and a genotype editing feature for editing the results of an automatic gel analysis. The system allows for manual and automatic analysis of the straightened gel image according to a specified set of analysis parameters providing a range of analysis stringency levels.

35 Claims, 25 Drawing Sheets

FIG. 4H

| Channel 1 | | Channel 2 | | Channel 3 | | Channel 4 | |
|---|---|---|---|---|---|---|---|
| Homozygous Cutoff | | Homozygous Cutoff | | Homozygous Cutoff | | Homozygous Cutoff | |
| 0.50 | | 0.00 | | 0.25 | | 0.07 | |
| Homozygous Hysteresis | | Homozygous Hysteresis | | Homozygous Hysteresis | | Homozygous Hysteresis | |
| 0.05 | | 0.00 | | 0.05 | | 0.00 | |
| NoCall Cutoff | | NoCall Cutoff | | NoCall Cutoff | | NoCall Cutoff | |
| 0.85 | | 0.00 | | 0.05 | | 0.00 | |
| Channel Threshold | | Channel Threshold | | Channel Threshold | | Channel Threshold | |
| 12000 | | 30000 | | 7500 | | 28000 | |
| Boost factor | | Boost factor | | Boost factor | | Boost factor | |
| 1.00 | | 1.00 | | 3.50 | | 2.50 | |
| MINHEIGHT | | MINWIDTH | | MAXHEIGHT | | MAXWIDTH | |
| 3.00 | | 5.00 | | 15.00 | | 25.00 | |
| Allele Threshold | | FixUp Offset | | | | | |
| 30000 | | 16 | | | | | |
| UPDATE | | DONE | | | | | |

File  Filter  Genotype  Display  Imagestack  Greymode

```
NSCANLINES: 2000
SCANLENGTH: 1250                    ← HEADER FILE
STARTSCANLINE: 1
ENDSCANLINE: 600
NUMCHANNELS: 4
SCANERRORLINES: 0
FIXUPOFFSET: 16
NSTDROWS: 3
NSTDCOLS: 16
NLNSBTWSTDLNS: 3
STDCHANNEL: 4
STDSIZE1: 139
STDSIZE2: 150
STDSIZE3: 160
MAXPIXELVALUE: 65535
ALLELETHRESH: 32000
ALLELE_MAXHT: 15
ALLELE_MAXWD: 25
ALLELE_MINHT: 3
ALLELE_MINWD: 5
NUMLANES: 61
CH1THRESHOLD: 32000
CH2THRESHOLD: 30000
CH3THRESHOLD: 7500
CH4THRESHOLD: 25000
CH1BOOST: 1.000000
CH2BOOST: 1.000000
CH3BOOST: 3.500000
CH4BOOST: 2.500000
INITIAL_DISPLAY_CHANNEL: 1
CHANNELMAP: 8
DYESEPMATRIX: 0
  1.901300  -2.245500   2.329400  -0.915600
 -0.823900   3.033100  -3.177000   0.449900
 -0.427000  -0.759900   2.112200  -0.472100
 -0.186900   0.431100  -0.765400   1.400500
ALLELES_IN_CH1: 3
HOMOZYGOUS_CUTOFF: .6
HOMOZYGOUS_HYSTERESIS: 0.05
NO_CALL_CUTOFF: .75
SIZE1: 152
SIZE2: 155
```

FIG. 6A

```
NSCANLINES: 600        ◄─── length of gel file
SCANLENGTH: 1250       ◄─── number of pixels per line
STARTSCANLINE: 1
ENDSCANLINE: 600
NUMCHANNELS: 4         ◄─── number of dye channels
SCANERRORLINES: 0      ◄─── used for fixing scanning errors from h/w
FIXUPOFFSET: 16
NSTDROWS: 4
NSTDCOLS: 15
NLNSBTWSTDLNS: 3       ◄─── describes the standard
STDCHANNEL: 4
STDSIZE0: 100            ╲508
STDSIZE1: 139
STDSIZE2: 150
STDSIZE3: 160
MAXPIXELVALUE: 65535
ALLELETHRESH: 30000
ALLELE_MAXHT: 15       ◄─── parameters for
ALLELE_MAXWD: 25            image enhancement filters
ALLELE_MINHT: 3          ╲540
ALLELE_MINWD: 4
NUMLANES: 57
CH1THRESHOLD: 32000
CH2THRESHOLD: 28000
CH3THRESHOLD: 7500
CH4THRESHOLD: 25000
CH0BOOST: 1.000000
CH1BOOST: 2.000000
CH2BOOST: 1.500000
CH3BOOST: 1.500000
INIT_CHANNEL: 1
STRAIGHTENED: 0
DYESEPMATRIX: 0
 0.4705    2.3804   -2.7822    0.1466   ◄─── separation matrix
 3.8980  -10.7588   11.2906   -1.9229
-0.6630   -2.0554    4.1082   -0.2565      ╲549
-0.6717    1.9915   -2.7734    1.5862
NUMBER_MARKERS: 1
ChannelMarker1: 3                         ◄─── information for genotyping
NUMBEROFALLELES1: 5
HOMOZYGOUS_CUTOFF: 0.500000
HOMOZYGOUS_HYSTERESIS: 0.050000   ╲569
NO_CALL_CUTOFF: 0.65
SIZE1: 121
SIZE2: 125
SIZE3: 129
SIZE4: 133
SIZE5: 137              FIG. 6B
```

METHODS AND APPARATUS FOR ANALYZING ELECTROPHORESIS GELS

BACKGROUND OF THE INVENTION

1. Field of the Invention

The invention relates generally to methods and apparatuses for improved visualization and reading of electrophoresis gels. In particular, the invention relates to a system and methods for straightening an electrophoresis gel image and analyzing electrophoresis gels following electrophoresis of biological materials. The invention further relates to a system and methods for automatic analysis or autogenotyping of electrophoresis gels following straightening of the gel image.

2. Background of the Related Art

Electrophoresis is an extremely important and widespread technique in biological research, biotechnology, and medical and agricultural sciences. The technique relies on the migration or movement of charged molecules through a solid matrix in an electric field, and is especially applicable to the analysis of biological polymers, and in particular, to proteins and nucleic acids (RNA and DNA). Thus, electrophoresis is widely used for a broad range of purposes, including: nucleic acid sequencing, diagnosis of genetic diseases, as well as DNA fingerprinting in forensic medicine, paternity/maternity testing, and identification of disaster victims.

During electrophoresis, the distance migrated through the electrophoresis matrix by a molecular species is dependent on a number of factors, including: the size of the molecule, the net charge on the molecule, and the strength of the electric field. The distance migrated is inversely related to molecular size, i.e. the larger the molecule the smaller the distance migrated. Therefore, electrophoresis of a number of molecules, or DNA fragments, of different sizes results in a corresponding number of bands located at a range of different distances along the gel.

Each band of DNA represents multiple copies of a DNA fragment of a particular size (i.e. of a particular number of nucleotides). The fact that DNA fragments having different numbers of nucleotides or base pairs possess different electrophoretic mobilities, forms the basis for all separations and analyses of DNA and DNA fragments by electrophoresis.

In order to determine the size (or number of nucleotides, expressed as base pairs, bp) of a DNA fragment in a particular band of an electrophoresis gel, it is necessary to include a number of DNA standards in one or more lanes of the electrophoresis gel.

DNA standards are fragments of DNA of known size. Comparison of the distance migrated by the DNA standards with the distance migrated by a DNA fragment to be analyzed, allows for the calculation of the size of DNA fragments to be analyzed. Thus, by the use of standards, distances migrated by the various bands of the DNA to be analyzed can be assigned to a particular molecular size or number of bp. In fact typically, a mixture of a number of different sized standard molecules are run on an electrophoresis gel to provide a series of bands, or a ladder, in which each band or rung of the ladder represents a known molecular size.

One problem with electrophoresis gels, which impairs manual reading and analysis of the gel image, and which prevents accurate automatic analysis by a device, such as a computer controlled device, is that the bands are irregularly or imperfectly formed during electrophoretic migration. For example, it is frequently the case that one or more bands in one or more lanes of the gel are curved or crooked. Consequently, two identical molecules or DNA fragments having the same number of base pairs, and in adjacent lanes of the gel may not be perfectly aligned and may show somewhat different distances of migration. Such aberrations in an electrophoretic image are particularly common at the edges of the gel.

Another common problem in analyzing electrophoresis gels is the tendency of one or more bands to appear faint or indistinct.

Due to the high throughput and immense numbers of electrophoretic analyses currently being performed worldwide, there is tremendous long-felt need for a system that can rapidly, reliably and reproducibly perform automatic analysis of electrophoresis gels.

SUMMARY OF THE INVENTION

The present invention, therefore, solves the problems discussed above by allowing for the rapid, accurate, and reproducible analysis of electrophoresis gels, either manually or automatically. In particular, the present invention allows for the input of an electrophoresis gel image into an input unit, and the straightening of the electrophoresis gel image to provide a gel image in which each lane of the gel is straight in the vertical direction (y coordinate) and in the horizontal direction (x coordinate). Furthermore, the present invention allows for the automatic assignment of analysis values to one or more bands of a straightened electrophoresis gel image, wherein the level of stringency or degree of certainty with which the computer assigns an analysis value may be varied over a given range of analysis parameters. By appropriate entry of analysis parameters, the system will never make an incorrect call during automatic analysis.

The instant invention overcomes the problems associated with manual and automatic reading and analysis of an electrophoretic gel, in part by providing apparatus and methods for automatically straightening the image of a gel. The instant invention further allows for the editing of an unstraightened gel image, e.g. the intuitive insertion of indistinct or missing bands, and for the manual and automatic analysis of the gel image. During automatic analysis of a gel image, the system makes a "call" for each band, the call being a numerical value assigned to a band based on its location in the gel image. The term "call" may include a no-call response by the system in which the system does not assign an analysis value to a band or particular region of the gel image. The instant invention also allows the operator to edit the automatic analysis of a gel.

It is therefore an object of the instant invention to provide a method and system for straightening an image of an electrophoresis gel.

It is another object of the instant invention to provide an automated method and system for straightening an image of an electrophoresis gel in both the horizontal and vertical directions.

It is another object of the instant invention to provide a method and system for editing an unstraightened electrophoresis gel image.

It is another object of the instant invention to provide a method and system for portraying a straightened gel image on a computer screen, wherein a pointing device pointing to a given band provides for the automatic assignment of an analysis value to that band.

It is another object of the instant invention to provide a method and system for editing a straightened electrophoresis gel image.

It is another object of the instant invention to provide a method and system for manual analysis of a straightened electrophoresis gel image.

It is another object of the instant invention to provide a method and system for automatic analysis of a straightened electrophoresis gel image.

It is another object of the instant invention to provide a method and system for manual and automatic analysis of a straightened electrophoresis gel image.

One advantage of the invention is that it can provide a straightened electrophoretic gel image which is more amenable to analysis.

Another advantage of the invention is that it allows interactive editing of an automatic analysis of an electrophoresis gel.

Another advantage of the invention is that it can provide an image of an electrophoretic gel which is more readily analyzed manually.

Another advantage of the invention is that it can provide a straightened image of an electrophoretic gel which can be accurately and reproducibly analyzed automatically.

A further advantage of the invention is that it can provide an image of an electrophoresis gel which has straight lanes in the y direction and straight bands in the x and y directions.

A further advantage of the invention is that it can provide a read-out on a computer screen of the lane number and DNA fragment size corresponding to the x and y coordinates, respectively, of the location of a pointing device arrow on the computer screen.

A still further advantage of the invention is that the analysis parameters can be set such that the system never makes an incorrect call or assignment of an analysis value to a band during analysis of an electrophoresis gel.

A still further advantage of the invention is that the system can perform automatic analysis of an electrophoresis gel in a period of a few seconds.

One feature of the invention is that it can analyze gels with an arbitrary number of different dyes to stain the bands of the electrophoresis gel.

Another feature of the invention is that it can use four separate channels for visualizing or viewing the electrophoresis gel image, wherein each channel is dye-specific, and each channel can be viewed separately.

Another feature of the invention is that it comprises a boost unit for boosting or increasing the intensity of each band stained by a four dye system to provide a clearer image of the electrophoresis gel.

Another feature of the invention is that it uses a computer algorithm to straighten the bands and lanes of an electrophoresis gel image.

Another feature of the invention is that various parameters which control automatic analysis of the gel can be adjusted by the operator.

Another feature of the invention is that various parameters which control automatic analysis of the gel can be set independently for each dye channel.

Still another feature of the invention is that a particular region of the gel or gel image can be selected by the operator for viewing and analysis of that region in isolation from other regions of the gel or gel image.

A further feature of the invention is that the stringency with which bands or alleles on the gel are called or assigned a particular value can be varied by the operator.

These and other objects, advantages, and features are accomplished by the provision of a system or apparatus for straightening an image of an electrophoresis gel, the system comprising input means for receiving raw data from the gel, output means functionally coupled to the input means the output means having a display means for displaying an image of the electrophoresis gel according to the received raw data, and straightening means functionally coupled to the display means for straightening the gel image.

These and other objects, advantages, and features are accomplished by the provision of a system or apparatus for straightening an image of an electrophoresis gel, the system including an input unit for receiving raw data from the gel, an output unit functionally coupled to the input unit the output unit having a display unit for displaying an image of the electrophoresis gel according to the received raw data, and a straightening unit functionally coupled to the display unit for straightening the gel image.

These and other objects, advantages, and features are accomplished by the provision of a system or apparatus for analyzing an image of an electrophoresis gel, the system including input means for receiving raw data from the gel, output means functionally coupled to the input means the output means having a display means for displaying an image of the electrophoresis gel according to the received raw data, straightening means functionally coupled to the display means for straightening the gel image, and analyzing means coupled to the display means for analyzing the gel image.

These and other objects, advantages, and features are accomplished by the provision of a system or apparatus for analyzing an image of an electrophoresis gel, the system including an input unit for receiving raw data from the gel, an output unit functionally coupled to the input unit the output unit having a display unit for displaying an image of the electrophoresis gel according to the received raw data, a straightening unit functionally coupled to the display unit for straightening the gel image, and an analyzing unit coupled to the display unit for analyzing the gel image.

These and other objects, advantages, and features are accomplished by the provision of a system or apparatus for straightening and analyzing an image of an electrophoresis gel, the system including an input unit for receiving raw data from the gel, an output unit functionally coupled to the input unit the output unit having a display unit for displaying an image of the electrophoresis gel according to the received raw data, a straightening unit functionally coupled to the display unit for straightening the gel image, and an analyzing unit coupled to the display unit for analyzing the gel image.

These and other objects, advantages, and features are accomplished by the provision of a method for displaying a gel image, including the steps of inputting raw data from the gel to the data receiving unit of the input unit, processing the received raw data, transferring the processed data to the output unit, and displaying the processed data as a gel image.

These and other objects, advantages, and features are accomplished by the provision of a method for displaying a straightened gel image, including the steps of inputting raw data from the gel to the data receiving unit of the input unit, processing the received raw data, transferring the processed data to the output unit, displaying the processed data as a raw or unstraightened gel image, straightening the unstraightened gel image in the vertical and horizontal directions to provide a straightened gel image, and displaying the straightened gel image.

These and other objects, advantages, and features are accomplished by the provision of a method for straightening an image of an electrophoresis gel, including the steps of inputting raw data from the gel, displaying an image of the electrophoresis gel according to the received raw data, and straightening the gel image.

These and other objects, advantages, and features are accomplished by the provision of a method for straightening an image of an electrophoresis gel, including the steps of inputting raw data from the gel, displaying an image of the electrophoresis gel according to the received raw data, locating the centers of at least two of the standard bands on the gel image, defining the coordinates of the centers of the at least two standard bands on the gel image, searching the gel image to locate the centers of each of the standard bands on the gel image, defining the coordinates of the centers of each of the standard bands on the gel image, comparing the actual coordinates or location of the centers of each of the standard bands on the gel image with the ideal coordinates of the centers of each of the standard bands on the image, calculating relocation factors for each pixel of the image, and relocating each pixel of each of the standard bands of the gel image to its ideal location or coordinates.

These and other objects, advantages, and features are further accomplished by the provision of a method for straightening a first image of an electrophoresis gel showing a plurality of genetic markers representing a plurality of different alleles, including the following steps: locating the centers of at least two of the standard bands on a second gel image showing a plurality of standard ladders, defining the coordinates of the centers of the at least two standard bands on the second gel image, searching the second gel image to locate the centers of each of the standard bands on the second gel image, defining the coordinates of the centers of each of the standard bands on the second gel image, comparing the actual coordinates or location of the centers of each of the standard bands on the second gel image with the ideal coordinates of the centers of each of the standard bands on the second gel image, calculating relocation factors for each pixel of the second gel image, and applying the relocation factors for each pixel of the second image to the first image to provide a straightened first gel image.

These and other objects, advantages, and features are accomplished by the provision of a method for analyzing an image of an electrophoresis gel, including the steps of inputting raw data from the gel, displaying an image of the electrophoresis gel according to the received raw data, straightening the gel image, and analyzing the gel image.

These and other objects, advantages, and features are accomplished by the provision of a method for straightening and analyzing an image of an electrophoresis gel, including the steps of inputting raw data from the gel, displaying an image of the electrophoresis gel according to the received raw data, straightening the gel image, and analyzing the gel image.

These and other objects, advantages, and features are accomplished by the provision of a method for analyzing an electrophoresis gel, including the steps of: detecting the presence of bands on a gel image according to a pre-defined set of detection parameters; determining the coordinates for the bands detected; determining intensity values for the bands detected; performing an analysis calculation based on the intensity and coordinates of the bands detected to provide a qualitative call on the bands detected and a determination of the size of a DNA fragment corresponding to each of the bands detected.

These and other objects, advantages, and features are also accomplished by the provision of a method for analyzing a gel image, including the steps of: monitoring the number of pixels or image size of each band and potential band of the gel image to provide a first set of data for each band and potential band for comparison with a pre-defined band image size parameter value; monitoring the intensity of each band and potential band on the gel image to provide a second set of data; comparing the intensity of each band and potential band with the average intensity of each band and potential band on the gel image to determine whether each band and potential band meets the pre-defined intensity parameters to be included in the analysis to provide a third set of data; monitoring the x and y coordinates of each band on the gel image to provide a fourth set of data; performing calculations on the first, second, third and fourth sets of data to determine the location and relative intensity of each band on the gel image; and assigning a numerical value to each band of the gel.

These and other objects, advantages, and features are further accomplished by the provision of a method for analyzing a gel image, including the steps of: monitoring the size of each band and potential band of the gel image to provide a first set of data for each band and potential band for comparison with a pre-defined band image size parameter value; monitoring the intensity of each band and potential band on the gel image to provide a second set of data; comparing the intensity of each band and potential band with the average intensity of each band and potential band on the gel image to determine whether each band and potential band meets the pre-defined intensity parameters to be included in the analysis to provide a third set of data; monitoring the x and y coordinates of each band on the gel image to provide a fourth set of data; comparing the intensity of intra-lane bands to provide a fifth set of data; performing calculations on the first, second, third, fourth and fifth sets of data to determine the location and relative intensity of each band on the gel image; and assigning a numerical value to each band on the gel image.

These and other objects, advantages, and features of the invention will become more apparent from the following description when the same is read in conjunction with the accompanying drawings.

BRIEF DESCRIPTION OF THE DRAWINGS

FIG. 4H is a computer screen in a gel analysis system showing an image of an electrophoresis gel overlaid by a window of the gel analysis software, the window for entry of parameters required for straightening the gel and automatic genotyping of the gel. The numerical display from 1 to 49 along the upper part of the screen indicates lane number 14 (marked by a superimposed dark square) as the position of the pointing device arrow.

FIG. 6A shows an example of a gel-type header file with values (parameters or attributes) assigned numbers to the gel variables (or attributes).

FIG. 6B shows how groups of variables or parameters are categorized within the header file.

DETAILED DESCRIPTION OF PREFERRED EMBODIMENTS

Figure 1A:
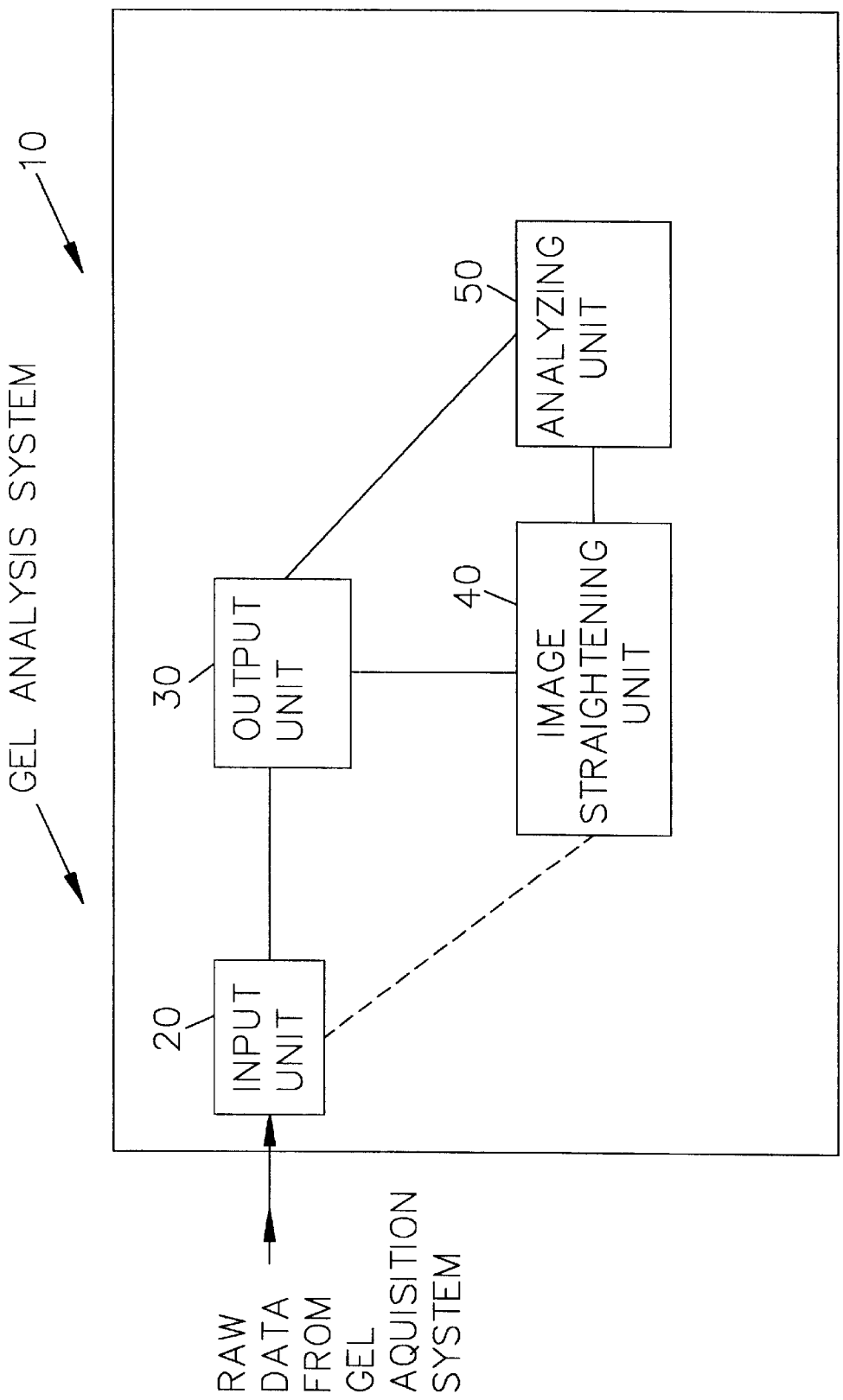
FIG. 1A shows a schematic representation of a gel analysis system according to one embodiment of the invention.

FIG. 1A shows a gel analysis system 10 according to one embodiment of the invention. Gel analysis system 10 includes an input unit 20 for receiving raw data from the electrophoresis gel acquisition system an image straightening unit or, straightening unit 40 for providing a straightened gel image, an output unit 30 for portraying the raw data from the electrophoresis gel and the straightened gel image, and an analyzing unit 50 for analyzing the data of the straightened gel image.

Raw data from an electrophoresis gel received by input unit 20 will typically be in the format of an image, but may also be in the form of a set of numeric data, or in other forms. Also, if desired, the raw data may be portrayed as an unstraightened image of the electrophoresis gel using output unit 30.

Input unit 20 can be any device capable of receiving raw data from a gel image acquisition system (not shown). For example, input unit 20 could be a MODEM, serial or parallel port, CD ROM, tape, or disk drive or any I/O port. It should be noted that input unit 10 can accept data acquired using any type of gel image acquisition system, and gel analysis system 10 can analyze this data, provided the appropriate information about the gel is also eventually input or already resident in system 10 as will be discussed in more detail below.

Image straightening unit 40 can be a dedicated hardware unit such as a processor, group of processors, or even a customized chip. Alternatively, image straightening unit 40 can be one of several processes running on a standard personal computer.

Analyzing unit 50 can also be a dedicated hardware unit such as a processor, group of processors, a customized chip, or one of several processes running on a standard personal computer.

Output unit 30 can be any type of display unit or printer. In a preferred embodiment, output unit 30 will normally include a CRT or liquid crystal display by which the operator may view a gel image, such as on a computer screen. Output unit 30 may also or alternatively include a display in the form of a hard copy print out of an image, or even simply a print out of text or numerical data.

Figure 4A:
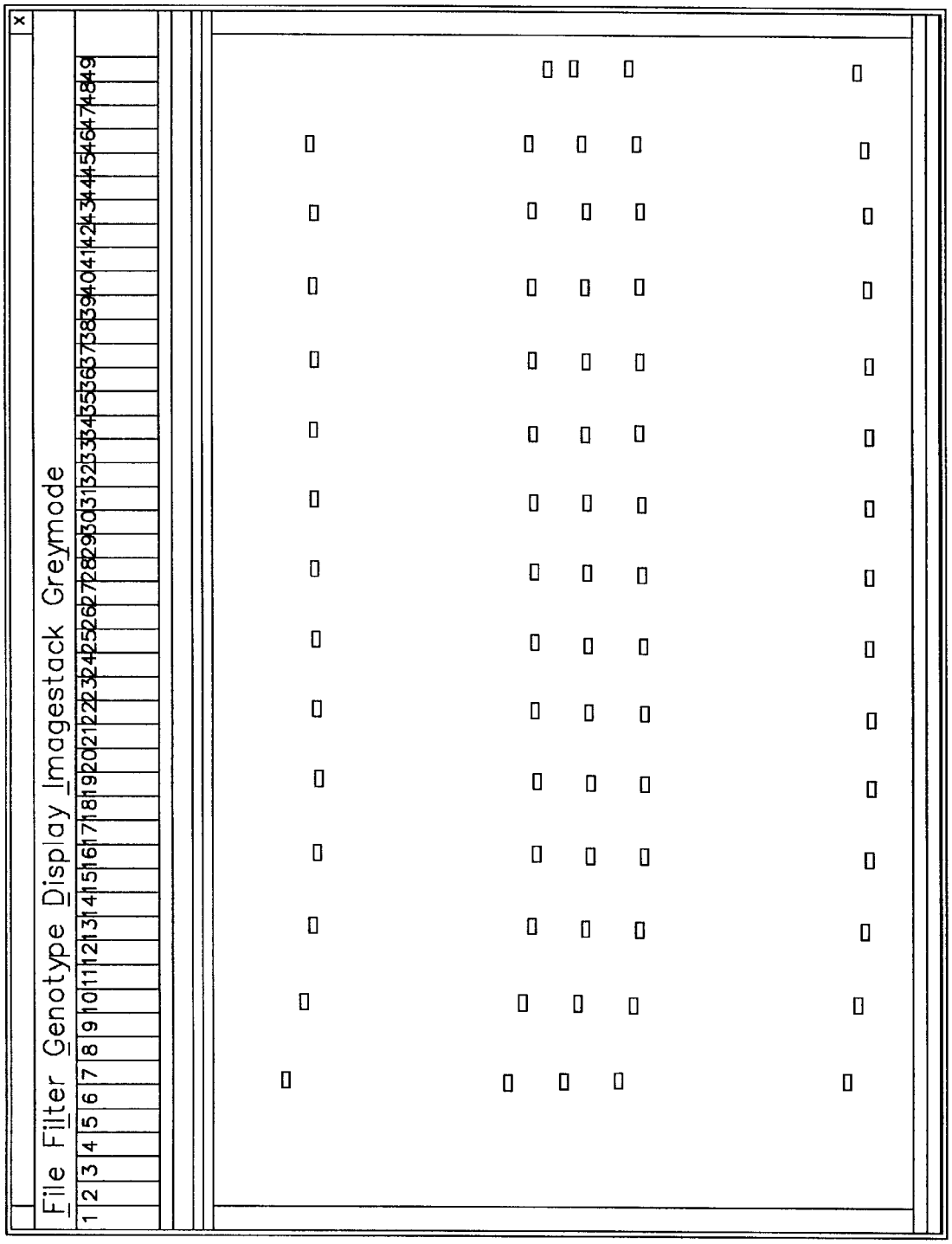
FIG. 4A is a computer screen in a gel analysis system showing an image of an electrophoresis gel in its raw or unstraightened form in which channel 4 is selected to selectively display lanes containing a series of bands of standard DNA fragments.

Image straightening unit 40 selects the standard channel or the channel of the standard from output unit 30, the standards which correspond to DNA fragments of known size are selectively displayed as a series of bands or ladders in multiple lanes of the gel (see, e.g., FIG. 4A). In one example, the series of bands representing the standard DNA occurs in every fourth lane of the gel. Straightening unit 40 uses the coordinates of a plurality of the standard bands as positional bases or reference coordinates for straightening each lane of the gel image both vertically and horizontally, in a process which is described in greater detail hereinbelow. According to one embodiment of the invention, output unit 30 displays a particular region or sub-image of the complete image of an electrophoresis gel. Display of sub-images allows the operator to focus the analysis on the particular regions of the gel of greatest interest.

When straightening unit 40 straightens the sub-image of the standard lanes of channel 4, it also straightens the same sub-image of the gel for the other dye channels. The straightened sub-image of channel 4 in turn allows analyzing unit 50 to analyze the electrophoresis gel. The analysis may be performed automatically and/or manually. That is to say, the analysis may be performed entirely manually; or the analysis may be performed entirely automatically; or, following automatic analysis, the automatic analysis of one or more regions of the gel image may be edited, revised, and/or re-analyzed interactively as will be discussed below. Following analysis, either manual or automatic, the results are displayed by output unit 30.

System 10 (as well as systems 10' and 10" discussed below) provides a graphical system for DNA genotyping and sequencing which is applicable to a digitized image of an electrophoresis gel. The system is capable of processing the image to boost the intensity of the bands of the gel image and to edit the image to replace faint, indistinct or invisible bands in an incomplete image by "drawing" a new band with the appropriate location and intensity. Once the gel image of the standard channel is complete, the gel image for all channels may then be straightened by the system, as described hereinbelow. A straightened gel image may then be analyzed manually, automatically (by the system), or by a combination of automatic and manual analysis.

During automatic analysis of an electrophoresis gel by system 10, one or more bands of a straightened electrophoresis gel image may be automatically assigned analysis values. The analysis value or call assigned to a given band is a function of the y coordinate of that band on the gel, which in turn is a function of the size of the molecule or DNA fragment which constitutes that band. The degree of stringency with which an analysis value is assigned to a band may be varied over a given range of analysis parameters. For example, the system may perform automatic genotyping of a number of human subjects whose DNA has been subject to gel electrophoresis to determine which allele(s) each subject has for a particular gene or set of genes, as described in greater detail hereinbelow.

Criteria used by system 10 to permit the straightening of the gel image and automatic analysis of the gel image include the following parameters: the number of lanes on the gel; the mapping of dyes to channels (and the separation matrix); standard ladder information; base pair sizes for marker genes or alleles; and a set of parameters related to image quality, namely homozygous cut-off, homozygous hysteresis, and background noise (or no-call) cut-off. The homozygous cut-off parameter specifies the relative intensity that two bands within a given lane must have for the system to call an allele homozygous. The homozygous hysteresis parameter specifies a bipolar range relative to the corresponding homozygous cut-off value to determine a minimum intensity range for an allele to be called homozygous. The operation of system 10 will be further discussed with respect to FIGS. 2–6, below.

Figure 1B:
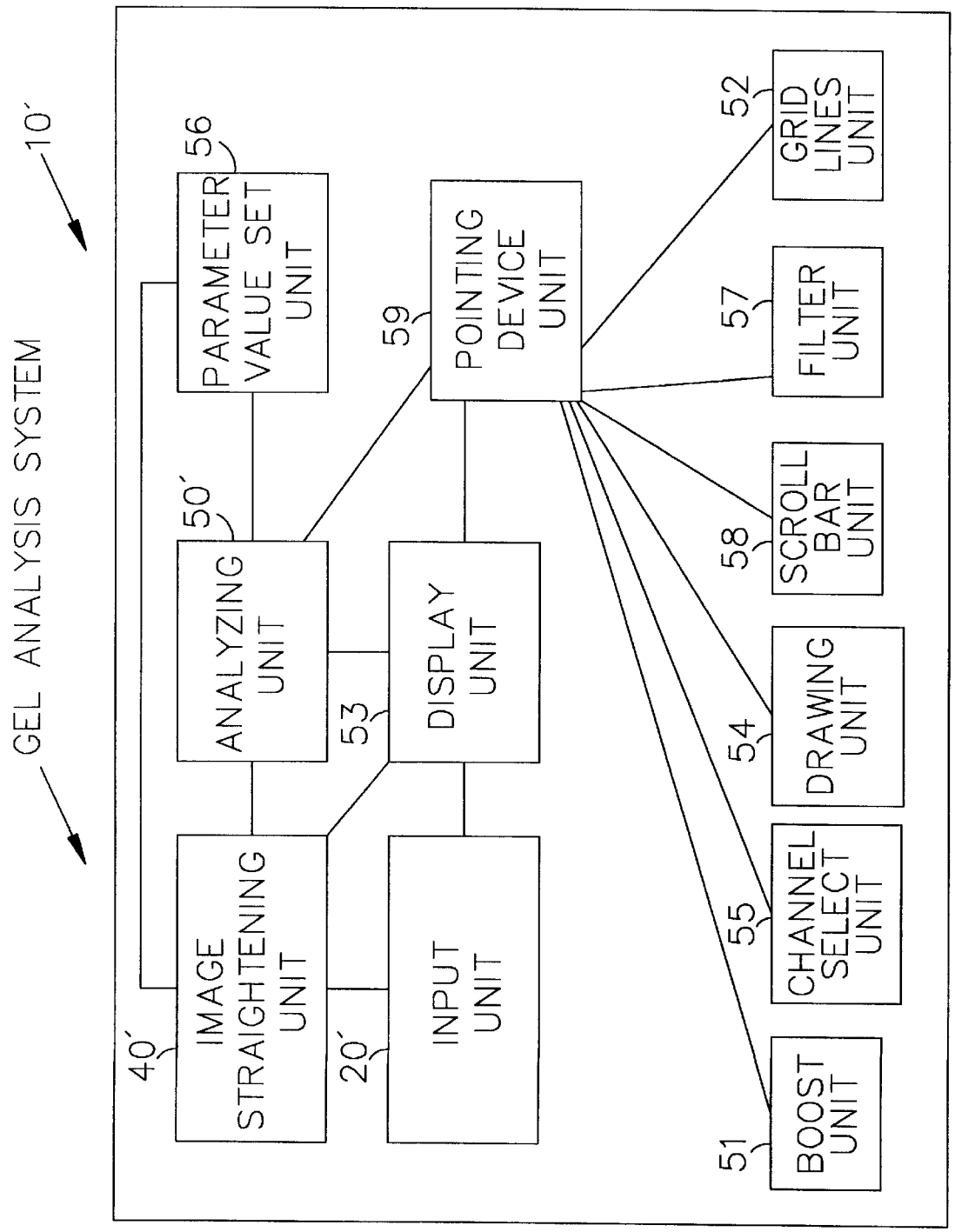
FIG. 1B shows a schematic representation of a gel analysis system according to another embodiment of the invention.

FIG. 1B shows a gel analysis system or unit 10' according to another embodiment of the invention. Throughout this specification, the use of primes after a number (e.g., 10') are meant to signify that the device is an alternative to the device referenced with an unprimed reference numeral. Unit 10' includes an input unit 20' for receiving raw data from the electrophoresis gel, an image straightening unit 40', and an analyzing unit 50'. Image straightening unit 40' is coupled to analyzing unit 50', both of which are coupled to display unit 53. Image straightening unit 40' may optionally be coupled to input unit 20'. Input unit 20' is analogous to input unit 20 of FIG. 1A, and can be any device capable of receiving raw data from a gel image acquisition system (not shown). For example, input unit 20' could be a MODEM, serial or parallel port, CD ROM, tape, or disk drive or any I/O port. Image straightening unit 40' can be a dedicated hardware unit such as a processor, group of processors, or even a customized chip. Alternatively, image straightening unit 40' can be one of several processes running on a standard personal computer. Analyzing unit 50' can include a dedicated hardware unit such as a processor, group of processors, a customized chip, or one of several processes running on a standard personal computer.

Gel analysis unit 10' further includes one or more of the following: a boost unit 51 for boosting the signal intensity of bands on the gel image; a display unit 53 for displaying an image of the gel; a parameter value set unit 56 for entry of parameters required for straightening the gel image and for automatic genotyping of the gel; a pointing device unit 59 for pointing to particular bands or locations of the displayed gel image; a channel select unit 55 for selecting a particular dye channel for viewing the gel image, a drawing unit 54 for selectively adding and subtracting elements of the displayed image; a scroll bar unit 58 for scrolling a read-out on the display unit; a filter unit 57 for adding and subtracting filters during processing of the gel image; and a grid lines unit 52 for providing grid lines on the gel image.

Display unit 53 may be a display screen, or a printer and can include a display in the form of a hard copy print out of an image, or even simply a print out of text or numerical data. In a preferred embodiment, display unit 53 may include a CRT or liquid crystal display by which the operator may view a gel image. Pointing device unit 59 can include a mouse and mouse pad, a trackball device, a pen or pen-like pointer adapted for pointing to specific location(s) on a CRT, liquid crystal display, or computer screen, or any suitable pointing device. Drawing unit 54 can include a mouse, a trackball device, or a pen adapted for pointing to specific location(s) on a computer screen; and can also include one of several processes running on a standard personal computer, or a customized and/or dedicated hardware unit. Each of scroll bar unit 58, parameter value set unit 56, filter unit 57, grid lines unit 52, boost unit 51, and channel select unit 55 can include a customized and/or dedicated hardware unit such as a processor, group of processors, or a customized chip, or one of several processes running on a standard personal computer, such as a PC.

The operation of system 10' will be further discussed with respect to FIGS. 2–6, below.

Figure 1C:
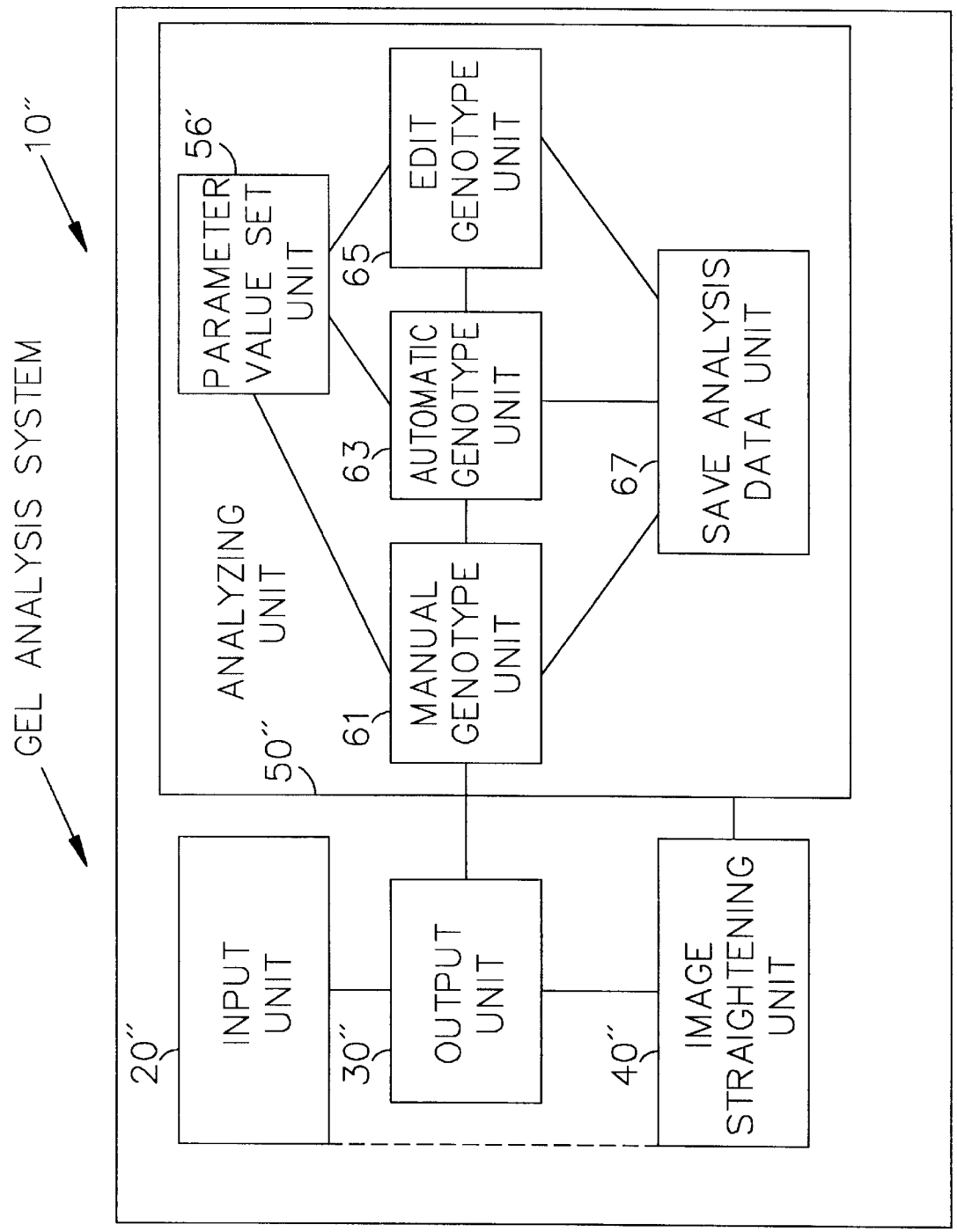
FIG. 1C shows a schematic representation of a gel analysis system according to yet another embodiment of the invention.

FIG. 1C shows another embodiment of the invention including a gel analysis system 10" which includes an input unit 20" for receiving raw data from the electrophoresis gel system, and an analyzing unit 50". Input unit 20" is analogous to input units 20 and 20' of FIGS. 1A and 1B, respectively, and input unit 20" can be any device capable of receiving raw data from a gel image acquisition system (not shown). For example, input unit 20" could be a MODEM, serial or parallel port, CD ROM, tape, or disk drive or any I/O port. Analyzing unit 50" includes a manual genotype unit 61 for manually analyzing a gel image or a sub-image thereof; an automatic genotype or autogenotype unit 63 for automatically analyzing a gel image or a sub-image thereof; an edit genotype unit 65 for editing data generated by the autogenotype unit; a parameter value set unit 56' for setting values for a plurality of analysis parameters; and a save analysis data unit 67 for saving analysis data generated by the analyzing unit 50. Each of manual genotype unit 61, automatic genotype or autogenotype unit 63, edit genotype unit 65, parameter value set unit 56', and save analysis data unit 67 can be one of several processes running on a standard personal computer, or a customized and/or dedicated hardware unit. The operation of system 10" will be further discussed with respect to FIGS. 2–6, below.

Figure 2A:
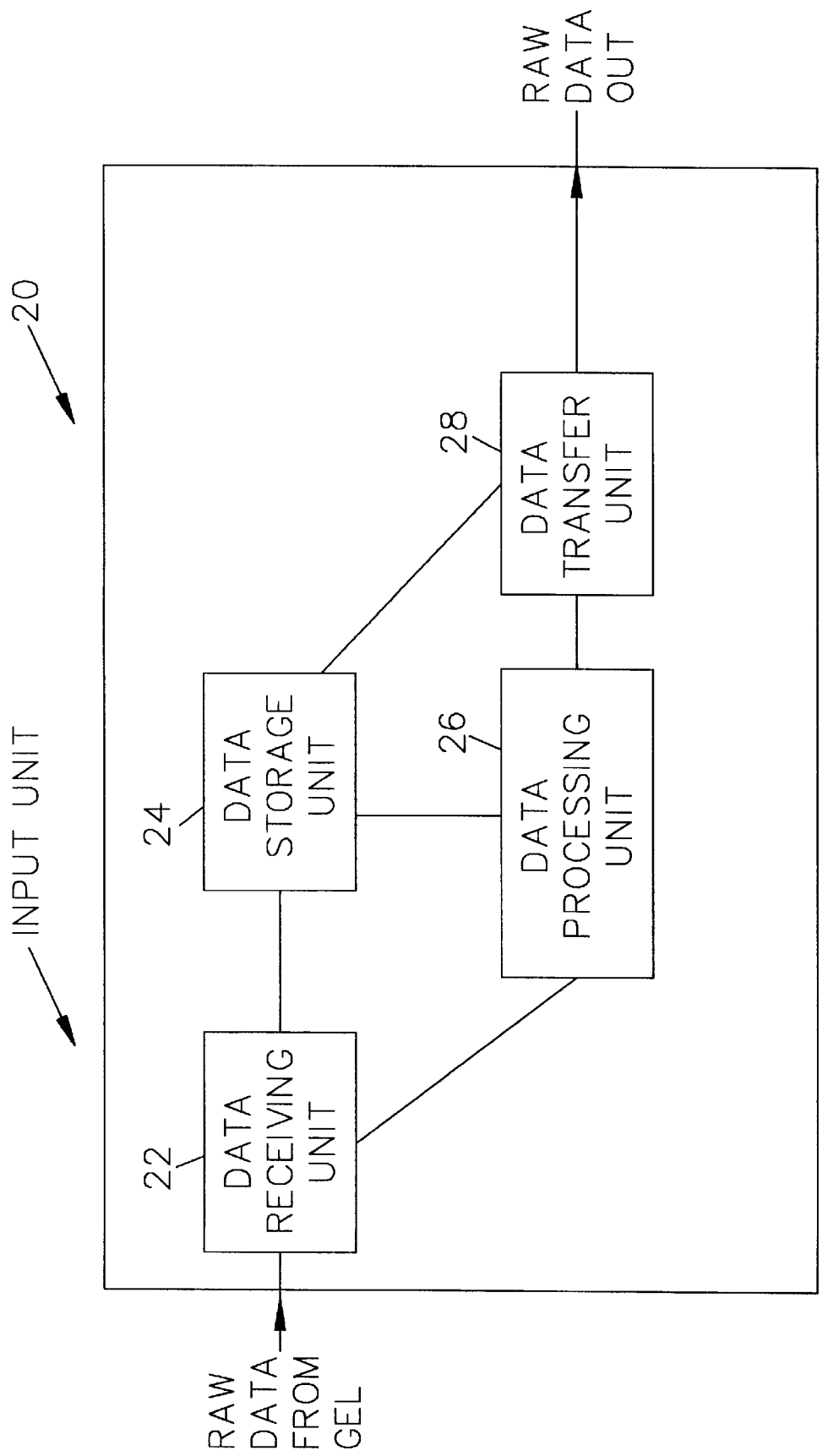
FIG. 2A shows a schematic representation of an input unit according to the present invention.

FIG. 2A shows an embodiment of input unit 20 in which raw data from an electrophoresis gel system for analysis is received by a data receiving unit 22. Input unit 20 further includes a data storage unit 24 for storing the raw data, and a data processing unit 26 for processing or converting the raw data to an alternative form, e.g. from numerical data to a gel image. Data storage unit 24 can include random access memory or a magnetic medium such as a hard disc of a standard personal computer, or any other form of data storage medium. Data processing unit 26 can be a customized chip, or a cpu of a standard personal computer. Both data storage unit 24 and data processing unit 26 are functionally coupled to data receiving unit 22. Input unit 20 further includes a data transfer unit 28, for transferring raw data to output unit 30 (not shown). Optionally, data transfer unit 28 may communicate directly with image straightening unit 40 (not shown). Data transfer unit 28 can be a simple computer bus. Output unit 30 is capable of transmitting raw data to image straightening unit 40 (FIG. 1A).

Figure 2B:
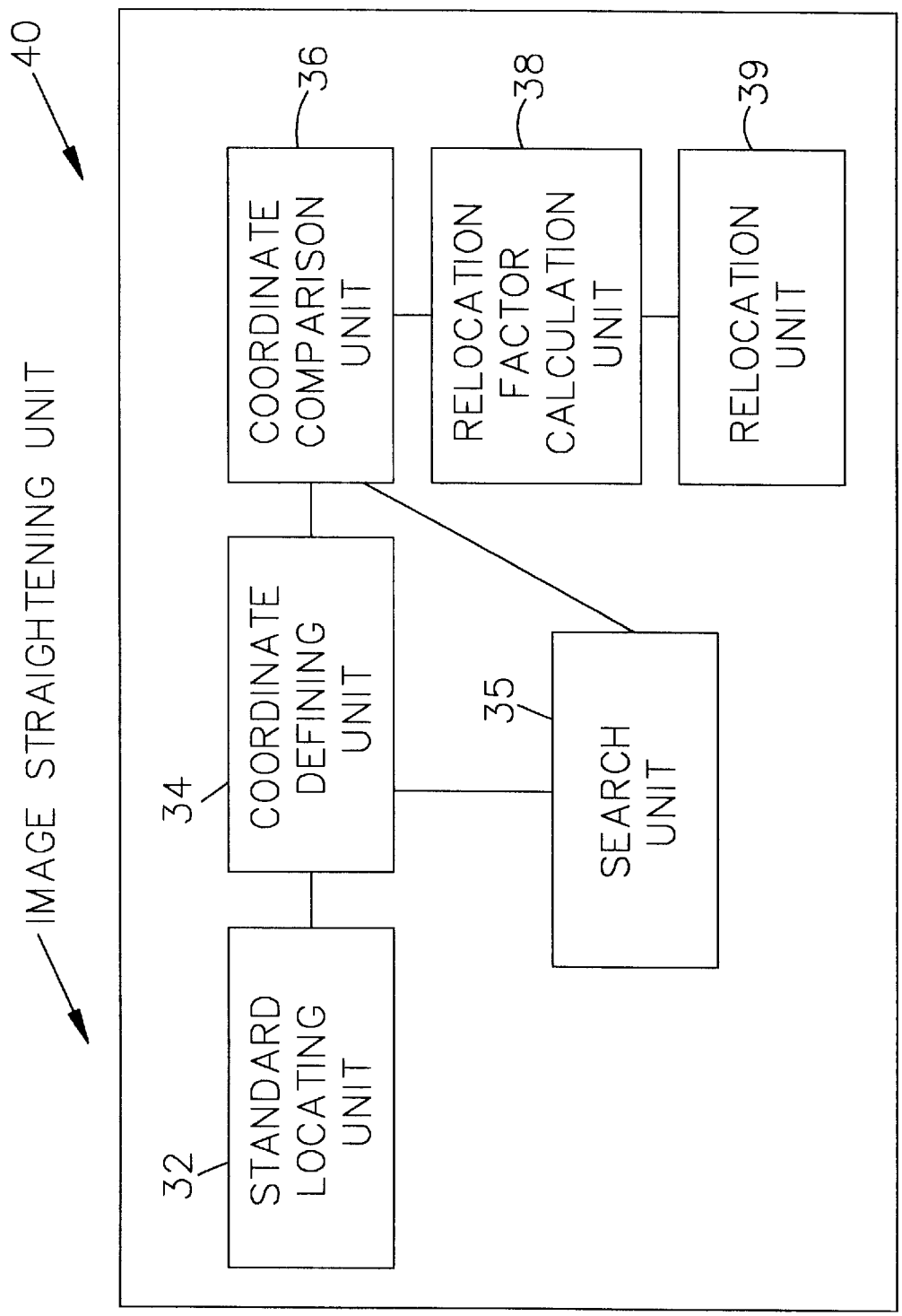
FIG. 2B shows a schematic representation of an image straightening unit according to the present invention.

FIG. 2B shows a schematic representation of image straightening unit 40 according to another embodiment of the invention, which includes a standards locating unit 32 for locating the centers of at least two of the standard bands of the gel image. The at least two standard bands may be at the same rung of the standard ladder and represent identical DNA fragments in at least two lanes or columns of the standards channel gel image. Standards locating unit 32 may include a pointing device, such as a mouse or track-ball operated device for pointing to a region or band of the gel image on a CRT or liquid crystal display. Standards locating unit 32 can also include one of several processes running on a standard personal computer, or a customized and/or dedicated hardware unit. Image straightening unit 40 further includes a coordinate defining unit 34, coupled to standards locating unit 32, for defining the x and y coordinates of the centers of the at least two standard bands of the gel image. Coordinate defining unit 34 can be one of several processes running on a standard personal computer, or a customized and/or dedicated hardware unit.

Image straightening unit 40 further includes a search unit 35, coupled to coordinate defining unit 34 for searching the gel image to locate the centers of each of the standard bands of the gel image. Search unit 35 cooperates with coordinate defining unit 34 to define the x and y coordinates of the centers of each of the standard bands of the gel image. Search unit 35 can be one of several processes running on a standard personal computer, or a customized and/or dedicated hardware unit.

Image straightening unit 40 further includes a coordinate comparison unit 36, coupled to both search unit 35 and coordinate defining unit 34, for comparing the actual coordinates or location of the centers of each of the standard bands of the gel image with the ideal coordinates of the centers of each of the standard bands on the image. Image straightening unit 40 further includes a relocation factor calculation unit 38, coupled to coordinate comparison unit 36, for calculating relocation factors, for each pixel of the image. Image straightening unit 40 still further includes a relocation unit 39, coupled to relocation factor calculation unit 38, for relocating each pixel of the standard bands gel image to its ideal location. Each of relocation factor calculation unit 38, coordinate comparison unit 36, and relocation unit 39 can be one of several processes running on a standard personal computer, or a customized and/or dedicated hardware unit.

Figure 2C:
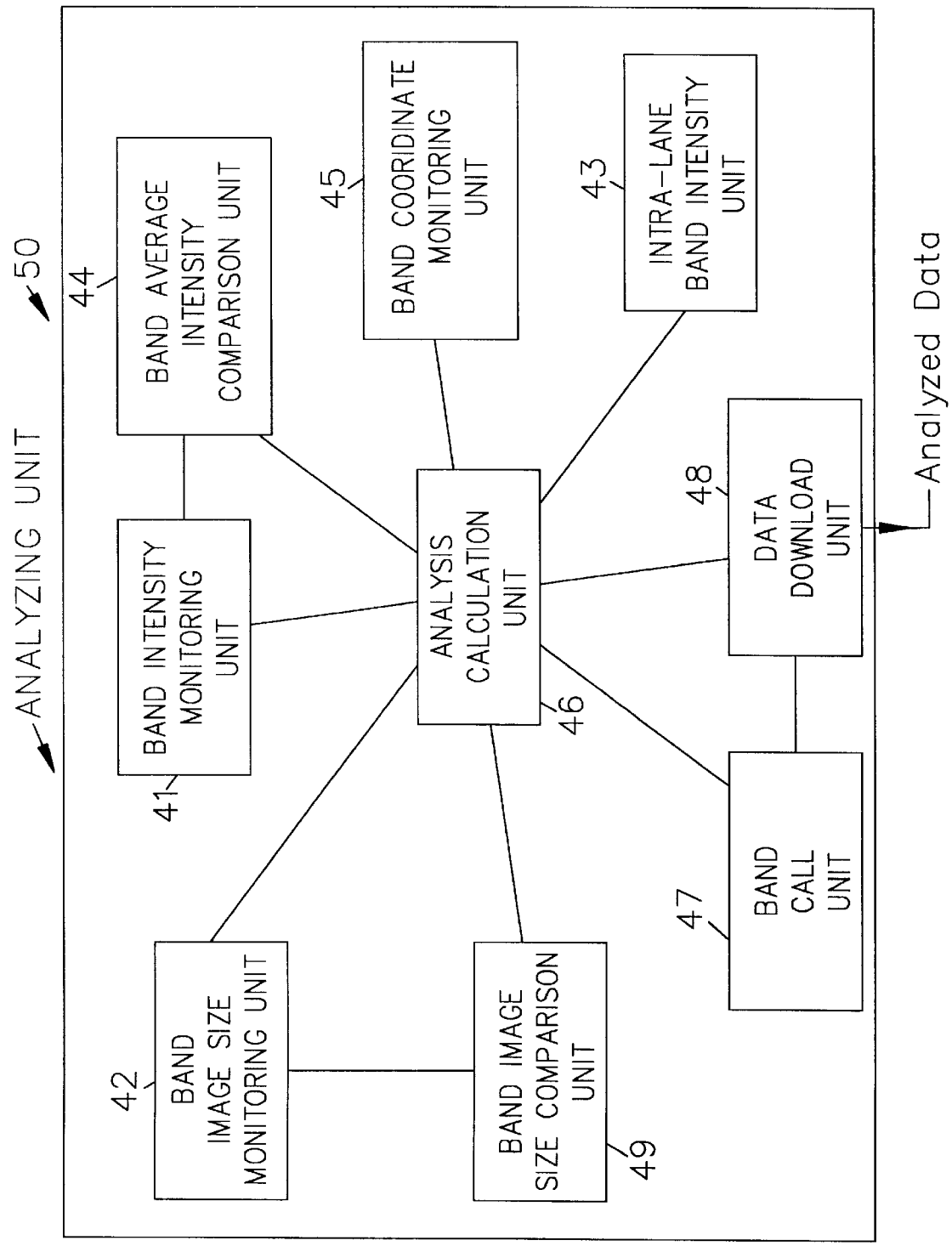
FIG. 2C shows a schematic representation of an analyzing unit according to the present invention.

FIG. 2C shows one embodiment of an analyzing unit 50 of the invention of gel analysis system 10. Analyzing unit 50 includes a band intensity monitoring unit 41 for monitoring the intensity of each band on a gel sub-image; a band image size monitoring unit 42 for monitoring the size of each band of the gel sub-image; a band image size comparison unit 49 for comparing the size of each band and potential band with a pre-defined band image size parameter value; an intra-lane band intensity comparison unit 43 for comparing the intensity of a first specific band with the intensity of a second specific band within the same lane of the gel; a band average intensity comparison unit 44 for comparing the intensity of each band with the average intensity of all bands in the gel sub-image; a band coordinate monitoring unit 45, for monitoring the x and y coordinates or locations of each band in the gel image; an analysis calculation unit 46, coupled to and receiving data input from the band image size monitoring unit 42, the band intensity monitoring unit 41, the intra-lane band intensity comparison unit 43, the band average intensity comparison unit 44 and the band coordinate monitoring unit 45, for providing calculated data as to the quality of each band of the gel image; a band call unit 47 for assigning a value to each band of the gel image; and a data download unit 48 which has the capacity to transfer analyzed data to an external device or to a computer database. Each of the band image size monitoring unit 42, the band intensity monitoring unit 41, the intra-lane band intensity comparison unit 43, the band average intensity comparison unit 44, the band coordinate monitoring unit 45, the analysis calculation unit 46, the band call unit 47, and the data download unit 48 can be one of several processes running on a standard personal computer, or a customized and/or dedicated hardware unit.

Figure 3A:
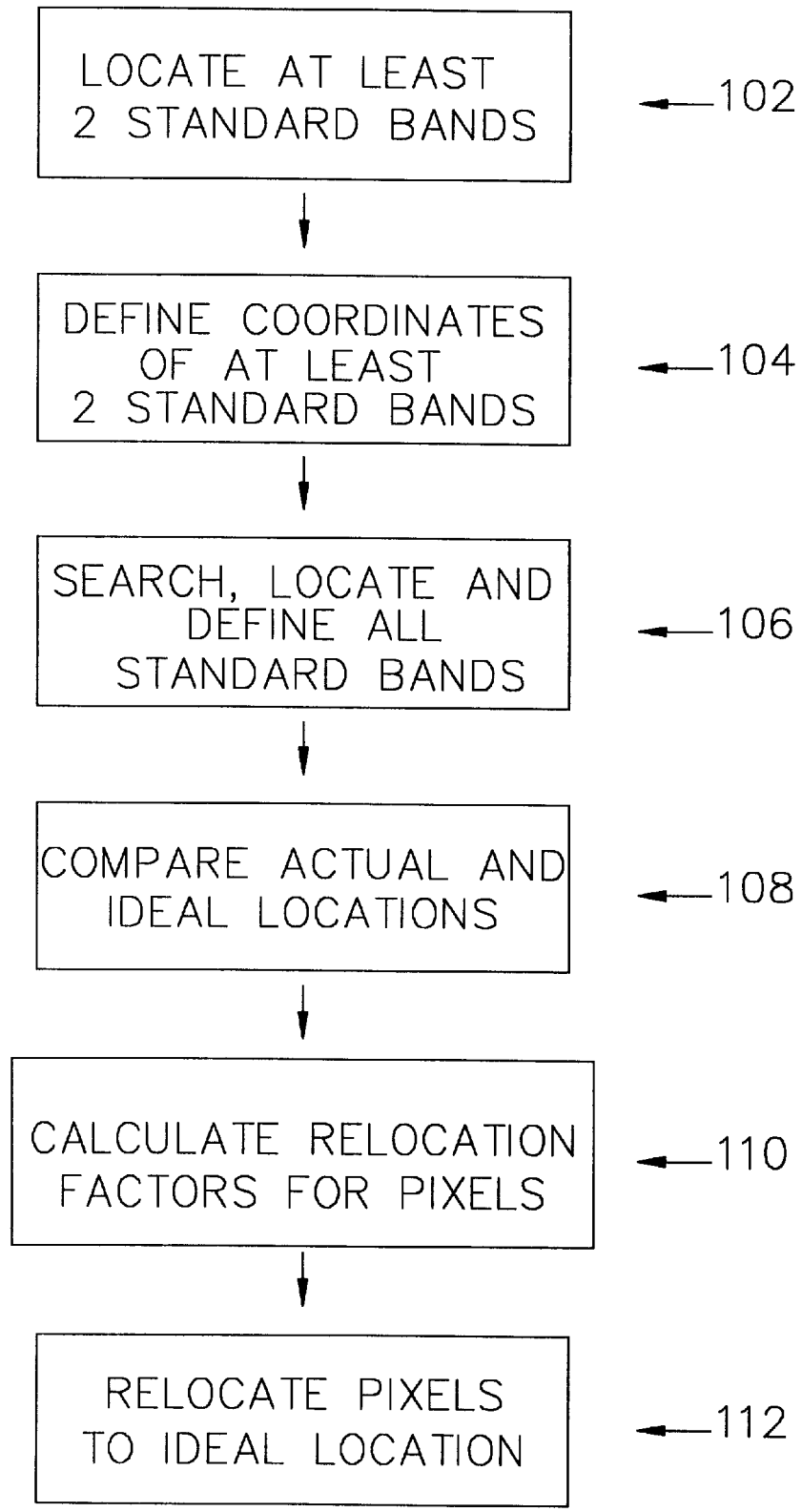
FIG. 3A shows steps in a gel image straightening method according to the instant invention.

FIG. 3A shows an embodiment of the invention relating to a method for straightening an image of an electrophoresis gel showing a plurality of standard ladders, which includes the following process steps. Step 102 includes locating the centers of at least two of the standard bands of the gel image by means of standards locating unit 32. Step 104 includes defining the x and y coordinates of the centers of the at least two standard bands of the gel image using coordinate defining unit 34. Step 106 includes searching the gel image using search unit 35 to locate the centers of each of the standard bands of the gel image, and defining the x and y coordinates of the centers of each of the standard bands of the gel image. Step 108 includes using the coordinate comparison unit 36 for comparing the actual coordinates or location of the centers of each of the standard bands of the gel image with the ideal coordinates of the centers of each of the standard bands on the image. Step 110 includes calculating relocation factors for each pixel of the image using the relocation factor calculation unit 38. Finally, step 112 includes relocating each pixel of each of the standard bands of the gel image to its ideal location by means of the relocation unit 39.

Figure 3B:
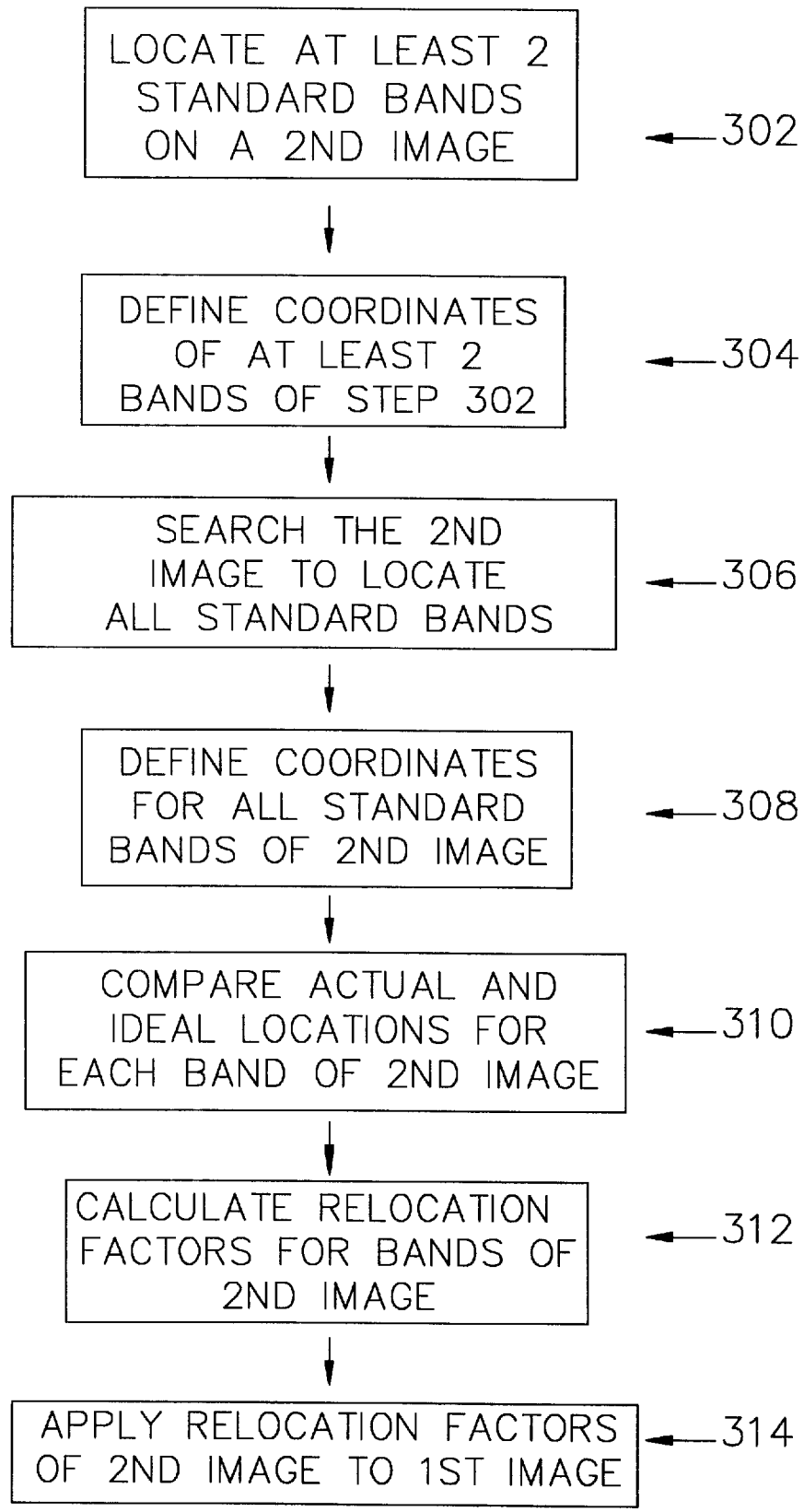
FIG. 3B shows steps in a gel image straightening method according to the invention.

FIG. 3B shows another embodiment of the invention relating to a method for straightening a first image of an electrophoresis gel showing a plurality of genetic markers representing a plurality of different alleles, including the following process steps. Step 302 involves locating the centers of at least two of the standard bands on a second gel image showing a plurality of standard ladders by means of standards locating unit 32. Step 304 involves using coordinate defining unit 34 for defining the x and y coordinates of the centers of the at least two standard bands on the second gel image. Step 306 involves using search unit 35 for searching the second gel image to locate the centers of each of the standard bands on the second gel image. Step 308 involves using coordinate defining unit 34 for defining the x and y coordinates of the centers of each of the standard bands on the second gel image. Step 310 includes using coordinate comparison unit 36 for comparing the actual coordinates or location of the centers of each of the standard bands on the second gel image with the ideal coordinates of the centers of each of the standard bands on the second gel image. Step 312 involves, by means of relocation factor calculation unit 38, calculating relocation factors for each pixel of the second gel image. Finally, step 314 involves, by means of relocation unit 39, applying the relocation factors for each pixel of the second image to the first image to provide a straightened first gel image.

Figure 3C:
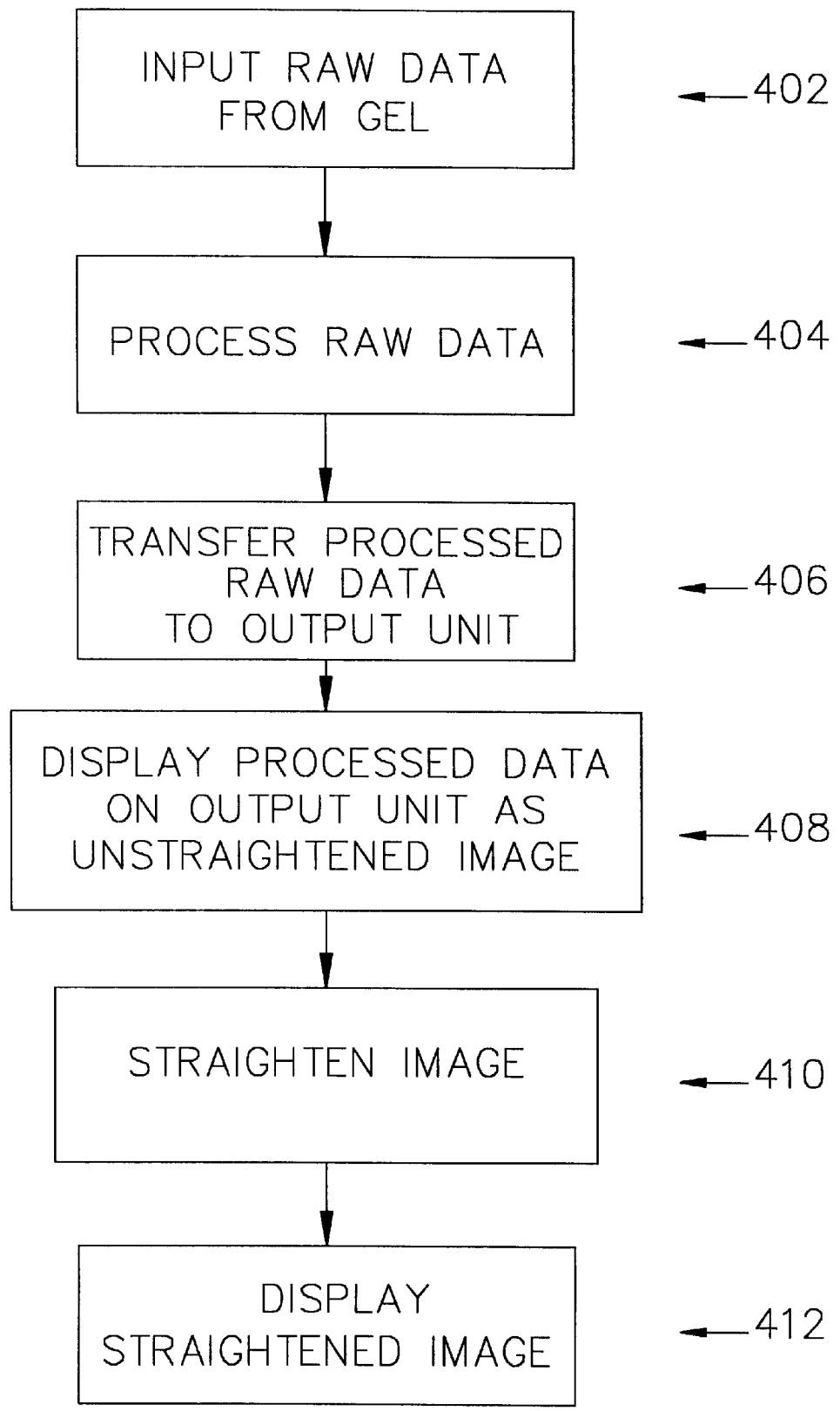
FIG. 3C shows steps in a method for displaying a straightened gel image according to the invention.

FIG. 3C shows a method according to another embodiment of the invention, including the following steps. Step 402 involves inputting raw data from the gel to data receiving unit 22 of input unit 20. Step 404 involves processing the received raw data using data processing unit 26. Step 406 involves transferring the processed data from step 404 to output unit 30 using data transfer unit 28. Step 408 involves displaying the processed data as a raw or unstraightened gel image on output unit 30 or display unit 53. Step 410 involves, by means of image straightening unit 40, 40' or 40", straightening the unstraightened gel image in the vertical and horizontal directions to provide a straightened gel image. Finally, step 412 involves displaying the straightened gel image on output unit 30 or display unit 53.

Figure 3D:
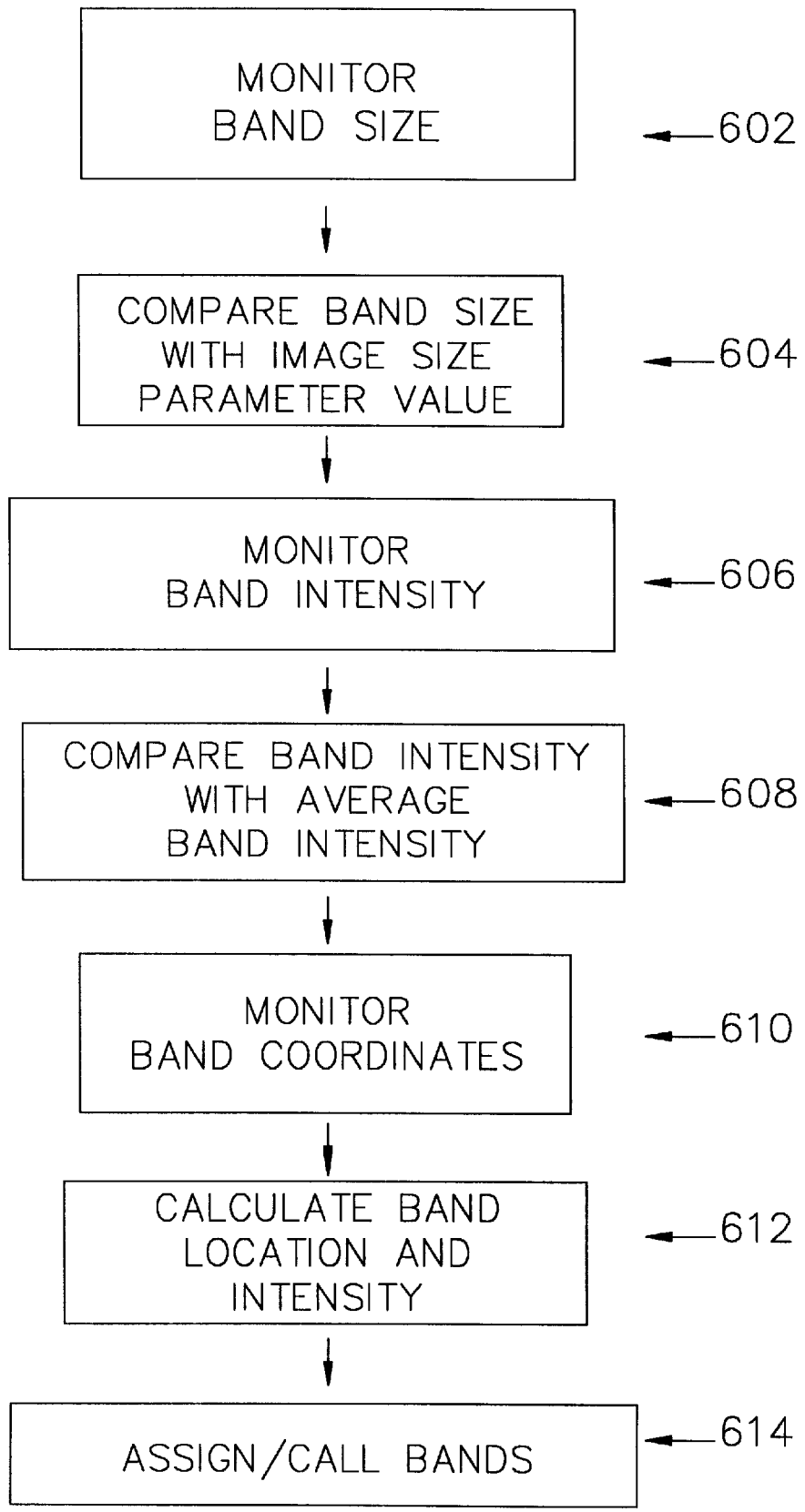
FIG. 3D shows steps in a gel analyzing method according to one embodiment of the invention.

FIG. 3D shows a method according to an embodiment of the invention, including the following steps. Step 602 involves monitoring the size of each band and potential band of the gel image using band image size monitoring unit 42 to provide a first set of data for each band and potential band. Step 604 involves using band image size comparison unit 49 for comparing the first set of data for each band and potential band with a pre-defined band image size parameter value to provide a second set of data. Step 606 involves monitoring the intensity of each band and potential band of the gel image using band intensity monitoring unit 41 to provide a third set of data. Step 608 involves using band average intensity comparison unit 44 for comparing the intensity of each band and potential band with the average intensity of each band and potential band of the gel image to determine whether each band and potential band meets the predefined intensity parameters to be included in the analysis to provide a fourth set of data. Step 610 involves the step of monitoring the x and y coordinates of each band of the gel image using band coordinate monitoring unit 45 to provide a fifth set of data. Step 612 involves the step of performing calculations on the first, second, third, fourth, and fifth sets of data using analysis calculation unit 46 to determine the location and relative intensity of each band of the gel image. Finally, step 614 involves using band call unit 47 for assigning a numerical value or call to each band of the gel image.

Figure 3E:
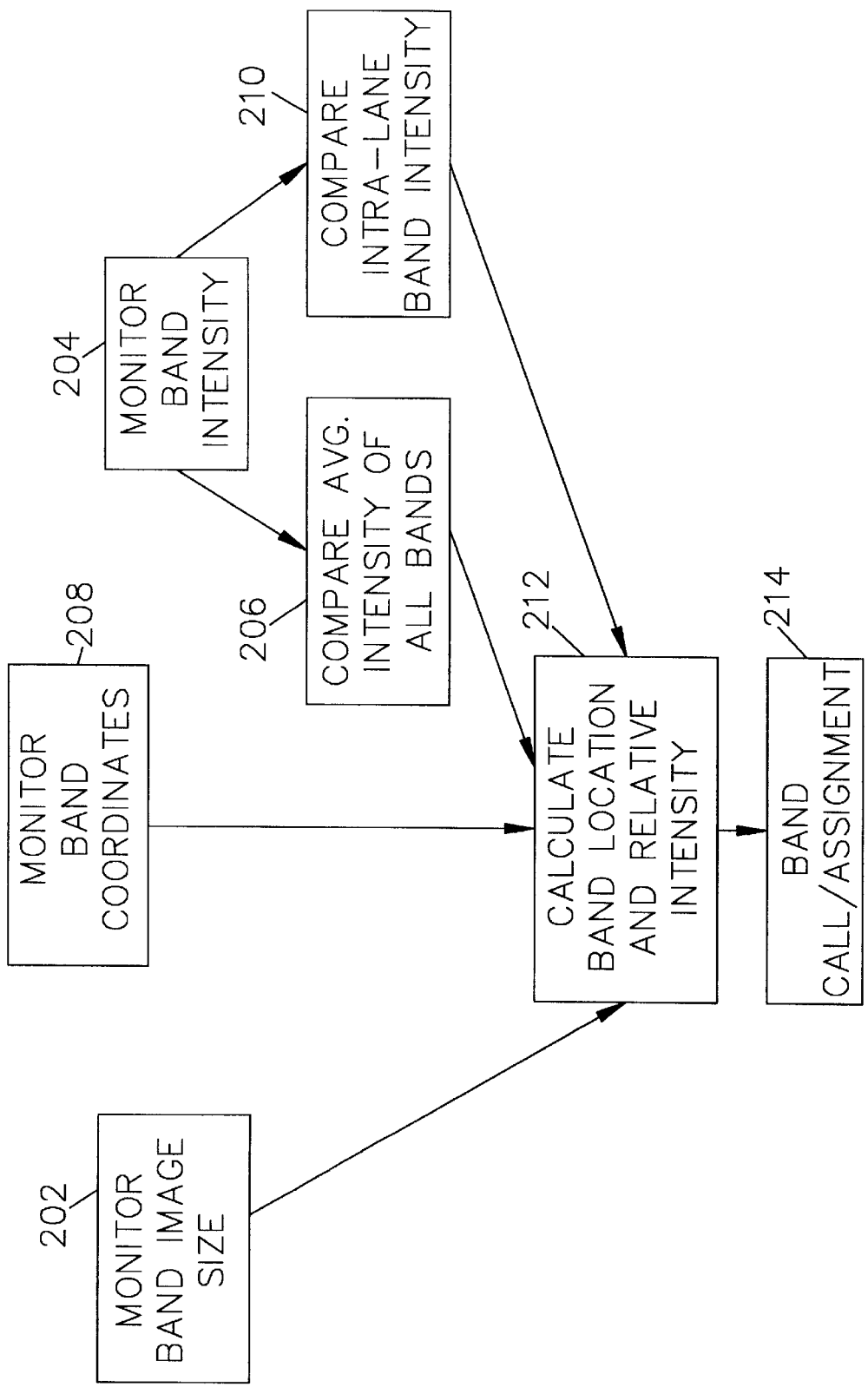
FIG. 3E shows steps in a gel analyzing method according to another embodiment of the instant invention.

FIG. 3E shows yet another embodiment of the invention relating to a method for analyzing a gel image, which includes the following process steps. Step 202 involves monitoring the size of each band and potential band of the gel image using band image size monitoring unit 42 to provide a first set of data for each band and potential band for comparison with a pre-defined band image size parameter value. Step 204 involves monitoring the intensity of each band and potential band of the gel image using band intensity monitoring unit 41 to provide a second set of data. Step 206 involves using band average intensity comparison unit 44 for comparing the intensity of each band and potential band with the average intensity of each band and potential band of the gel image to determine whether each band and potential band meets the pre-defined intensity parameters to be included in the analysis to provide a third set of data. Step 208 involves monitoring the x and y coordinates of each band of the gel image using band coordinate monitoring unit 45 to provide a fourth set of data. Step 210 involves comparing the intensity of intra-lane bands using intra-lane band intensity comparison unit 43 to provide a fifth set of data. Step 212 involves performing calculations on the first, second, third, fourth and fifth sets of data using analysis calculation unit 46 to determine the location and relative intensity of each band of the gel image. Finally, step 214 involves using band call unit 47 for assigning a numerical value to each band of the gel image.

The system will now be illustrated with reference to an embodiment of gel analysis system 10 and in the context of its use for the genetic analysis of a number of subjects for a particular gene for which there are a plurality of different forms of the gene or alleles. There are a pair of alleles in each lane, and each subject has either two different alleles for the particular gene (heterozygous subjects) or two identical alleles for the particular gene (homozygous subjects). Each allele in heterozygous subjects occupies a position between a different pair of horizontal grid lines on the gel image, and the position between each pair of horizontal grid lines on the gel image corresponds to a numerical call for one allele.

After a gel image in raw form has been loaded into input unit 20, such as the memory of a computer, the image may be displayed on output unit 30. Output unit 30 can be, for example, a color or monochrome monitor of a standard personal computer. A particular region of the gel image, or sub-image, may be displayed on an output unit 30 or display unit 53 to show a region of the gel of interest. Any one of four channels may be selected using the channel select unit 55. Each of the four channels corresponds to one of the four dyes used to stain the bands on the gel. In one embodiment of the invention, any one of the four channels may be selected from the upper right corner of a computer screen display; a dark square surrounding a channel number on the screen indicates the channel number that is selected.

Figure 4B:
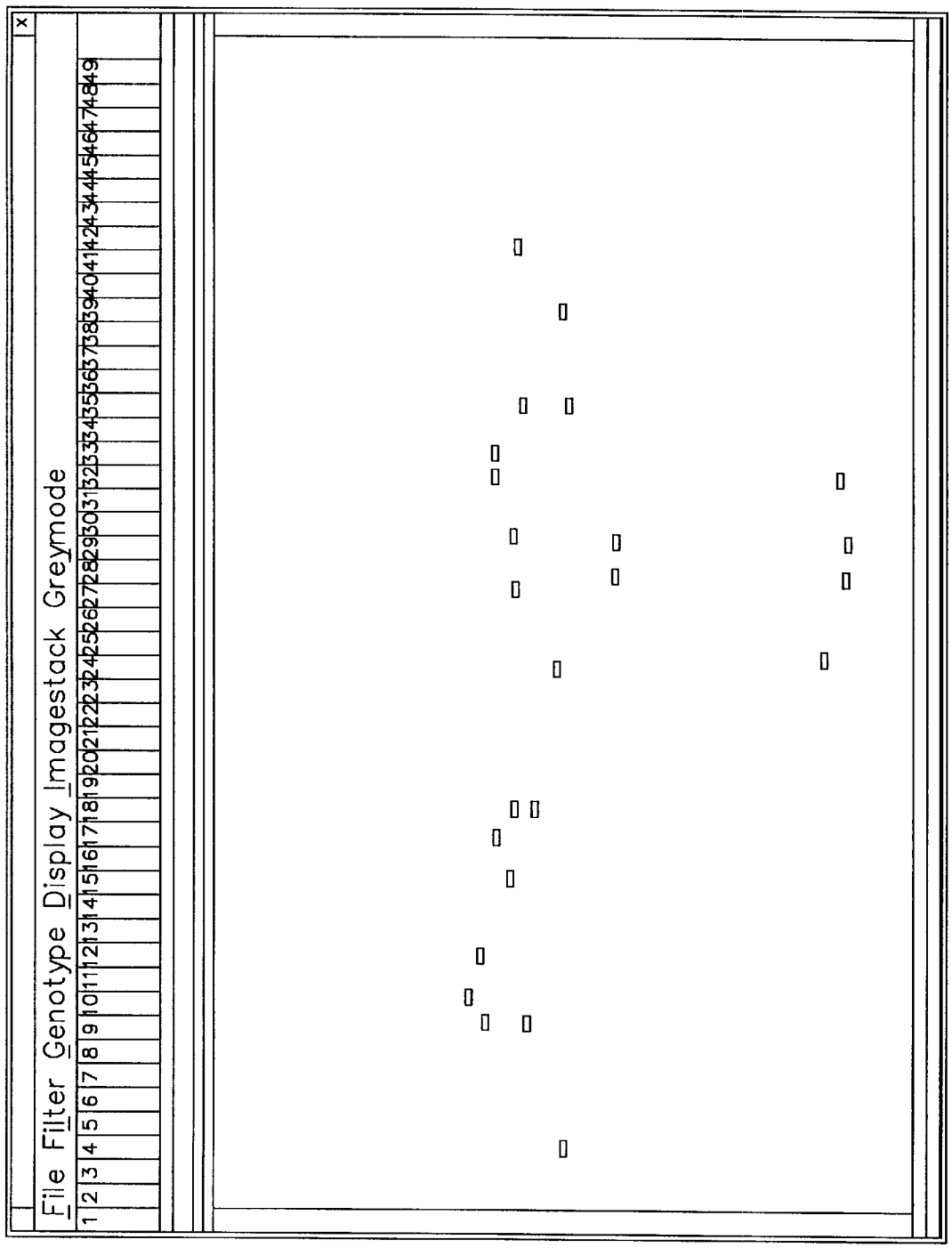
FIG. 4B is a computer screen in a gel analysis system showing the same sub-image or region of the same electrophoresis gel as in FIG. 4A in its unstraightened form, but in which channel 1 is selected to selectively display lanes containing DNA samples to be analyzed.

FIG. 4A shows a display unit of the instant invention, in the form of a computer screen in which the gel analysis system is displaying an image of an electrophoresis gel in its raw or unstraightened form and in which channel 4 is selected to selectively display lanes containing a series of bands of standard DNA fragments. The standards occur in every fourth lane of the gel in a total of 15 lanes or columns. FIG. 4B shows a display unit in the form of a computer screen in which the gel analysis system is displaying the same sub-image or region of the same electrophoresis gel as in FIG. 4A in its raw or unstraightened form, but in which channel 1 is selected to selectively display lanes containing DNA samples to be analyzed.

In the present example, there are seven standard bands (only five of which can be seen in the particular region of the gel displayed in FIG. 4A) each band corresponding to DNA fragments of a different size, ranging from 135 bp to 177 bp, in the region or sub-image of interest. The image on output unit 30 or display unit 53 may be viewed by the operator to determine whether the sub-image of the standards is complete, i.e. that every band or rung of the standard ladder is present and in the expected location.

Figure 4C:
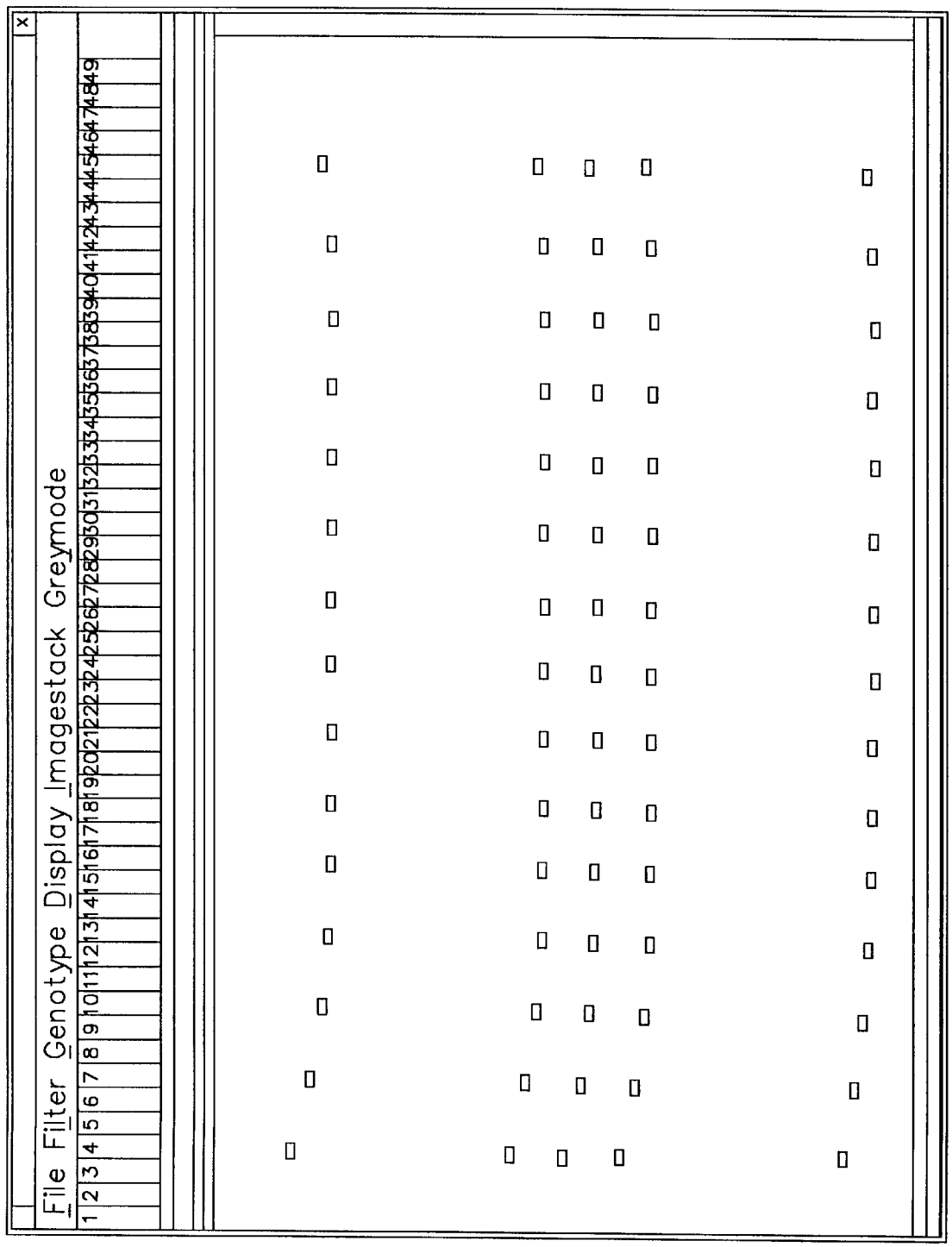
FIG. 4C is a computer screen in a gel analysis system showing an image of an electrophoresis gel in its unstraightened form in which channel 4 is selected, as in FIG. 4A, but with the Boost FTHR Dyes feature activated.

In order to assist the operator in viewing the image, the system has the ability to boost the signal from the dyes using boost unit 51. In a preferred embodiment of the invention, boost unit 51 can be activated simply by selecting the option "Boost FTHR Dyes" from the Filter menu of the gel analysis system 10, 10', or 10". FIG. 4C shows display unit 53 or a computer screen in the gel analysis system 10, 10' or 10" displaying an image of an electrophoresis gel in its raw or unstraightened form in which channel 4 is selected with the Boost Dyes feature activated to boost the standard channel dyes and to increase signal intensity of standard bands in the gel image.

Figure 4D:
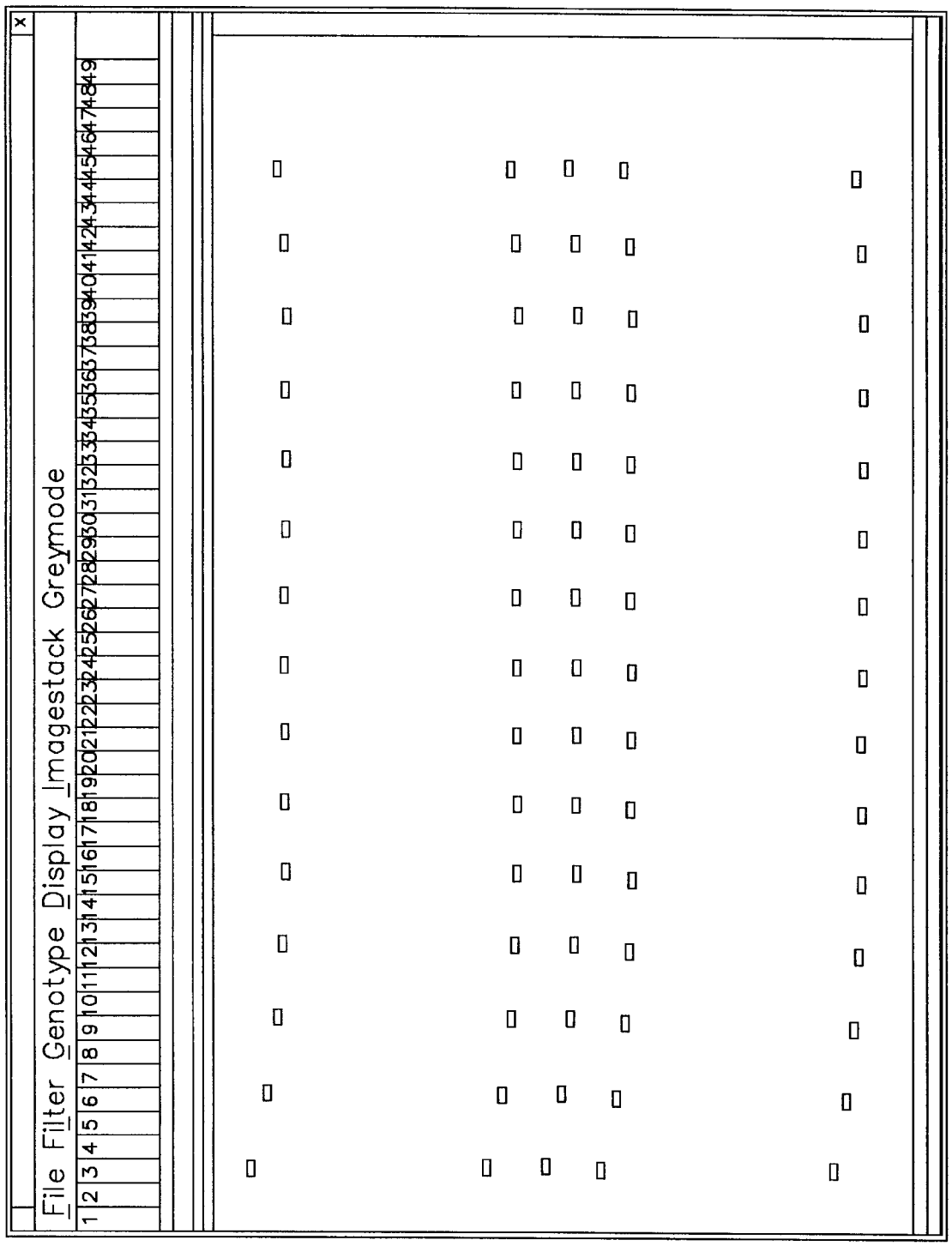
FIG. 4D is a computer screen in a gel analysis system showing an image of an electrophoresis gel in its unstraightened form in which channel 4 is selected to selectively display lanes containing a series of bands of standard DNA fragments, as in FIG. 4C, but with faint or missing bands of FIG. 4C redrawn as "perfect alleles".

The sub-image of the standards must be complete in order for the system to straighten the image via image straightening unit 40, 40'. In turn, as discussed elsewhere herein, the gel image must be straightened in order for the system to perform analysis of the gel via gel analyzing unit 50, 50'. Consequently, if one or more of the standard bands is not visible as a distinct band or is not in the expected location those bands must be inserted in the image or drawn in as "perfect alleles", for example, by means of drawing unit 54. In a preferred embodiment, such indistinct or misplaced bands may be drawn in by selecting "Draw Perfect Allele" from the Draw Mode menu. FIG. 4D shows display unit 53 or a computer screen in the gel analysis system 10, 10', or 10" showing an image of an electrophoresis gel in its raw or unstraightened form in which channel 4 is selected to selectively display lanes containing a series of bands of standard DNA fragments, as in FIG. 4C, but with faint or missing bands on the far right lane of the image of FIG. 4C redrawn as "perfect alleles".

Once the sub-image of interest showing the standard ladders (channel 4) is complete (15 lanes X seven bands), the image for all four channels may be straightened vertically and horizontally by means of image straightening unit 40, 40". By means of standards locating unit 32 the gel analysis system locates each of the standard bands on the unstraightened gel image. Coordinate defining unit 34 defines the coordinates for each of the standard bands of the unstraightened gel image. Coordinate comparison unit 34 compares the actual coordinates of the center of each of the standard bands of the gel image with the ideal coordinates of the center of each of the standard bands on the image. Relocation factor calculation unit 38 calculates relocation factors for each pixel of the image. Relocation factor calculator unit 38 applies the relocation factors for each pixel of the image to display unit 53 to provide a straightened gel image.

In a preferred embodiment of the invention including the gel analysis system 10, 10', or 10", image straightening is carried out as follows. The operator selects "Gel Straightening" from the Filter menu, and is prompted by a dialog box to select the band at the lower left corner of the sub-image displayed on the screen by pointing and clicking using a pointing device, such as a mouse or track-ball. The dialog box then prompts the operator to select the band at the lower right corner of the sub-image displayed on the screen, again by pointing and clicking using the pointing device. The system then automatically searches the entire sub-image and determines the coordinates for the center of each of the 105 (15×7) bands on the sub-image, compares the actual coordinates of the center of each of the standard bands of the gel image with the ideal coordinates of the center of each of the standard bands on the image, calculates relocation factors for each pixel of the image, and applies the relocation factors for each pixel of the image to the display unit to provide a straightened gel image.

Figure 4E:
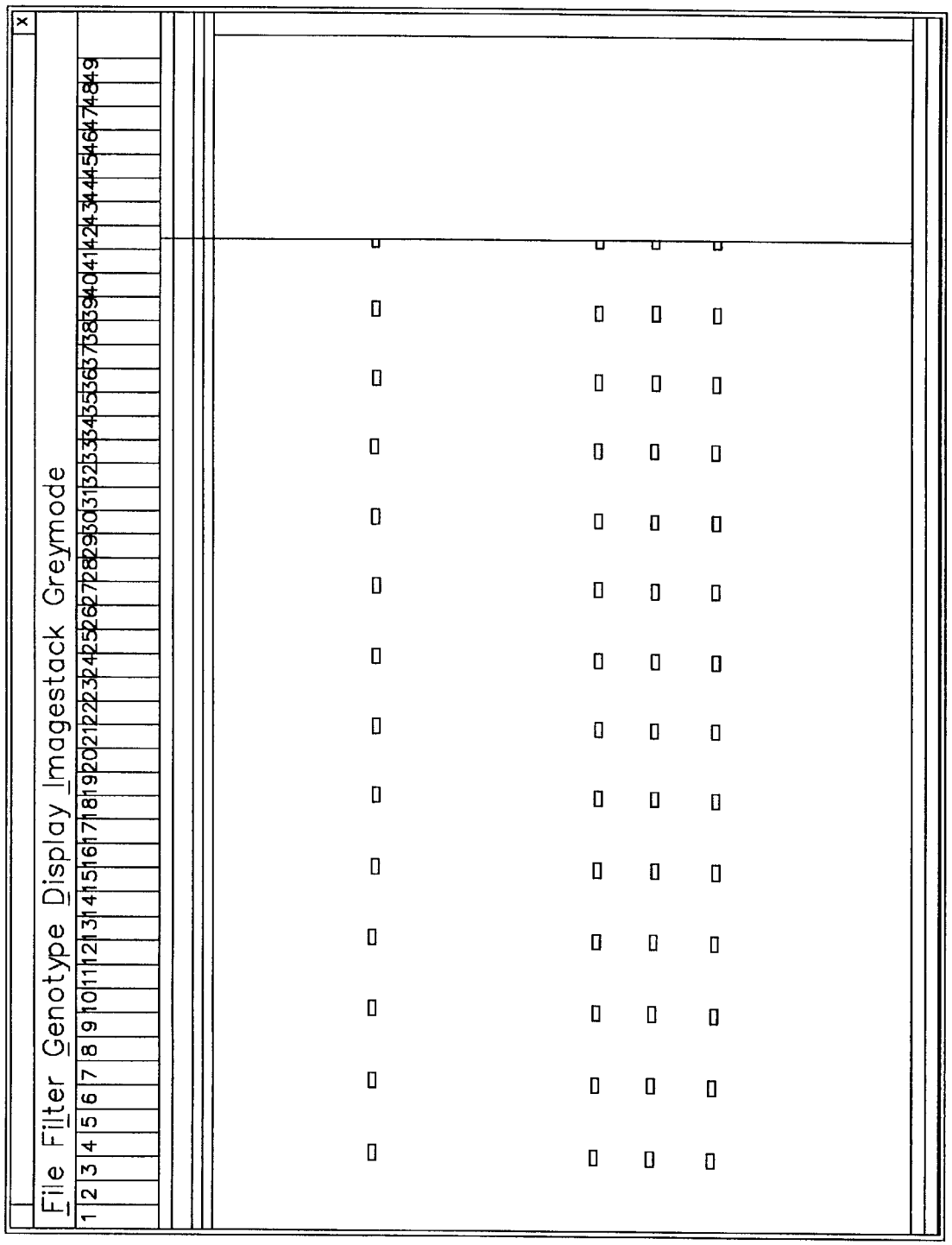
FIG. 4E is a computer screen in a gel analysis system showing an image of an electrophoresis gel in which channel 4 is selected to selectively display lanes containing a series of bands of standard DNA fragments, as in FIG. 4A, but with the lanes having been straightened vertically and horizontally.

FIG. 4E shows a computer screen of the gel analysis system 10 displaying an image of an electrophoresis gel, in which channel 4 is selected to selectively display lanes containing a series of bands of standard DNA fragments, and in which the lanes have been straightened vertically and horizontally by the image straightening unit.

The above method for straightening a gel image provides, inter alia, a pointing device location calibration feature by which the system reads and displays the pointing device arrow y coordinate as a DNA fragment size in base pairs (bp), and reads and displays the pointing device arrow x coordinate as a lane number.

Figure 4F:
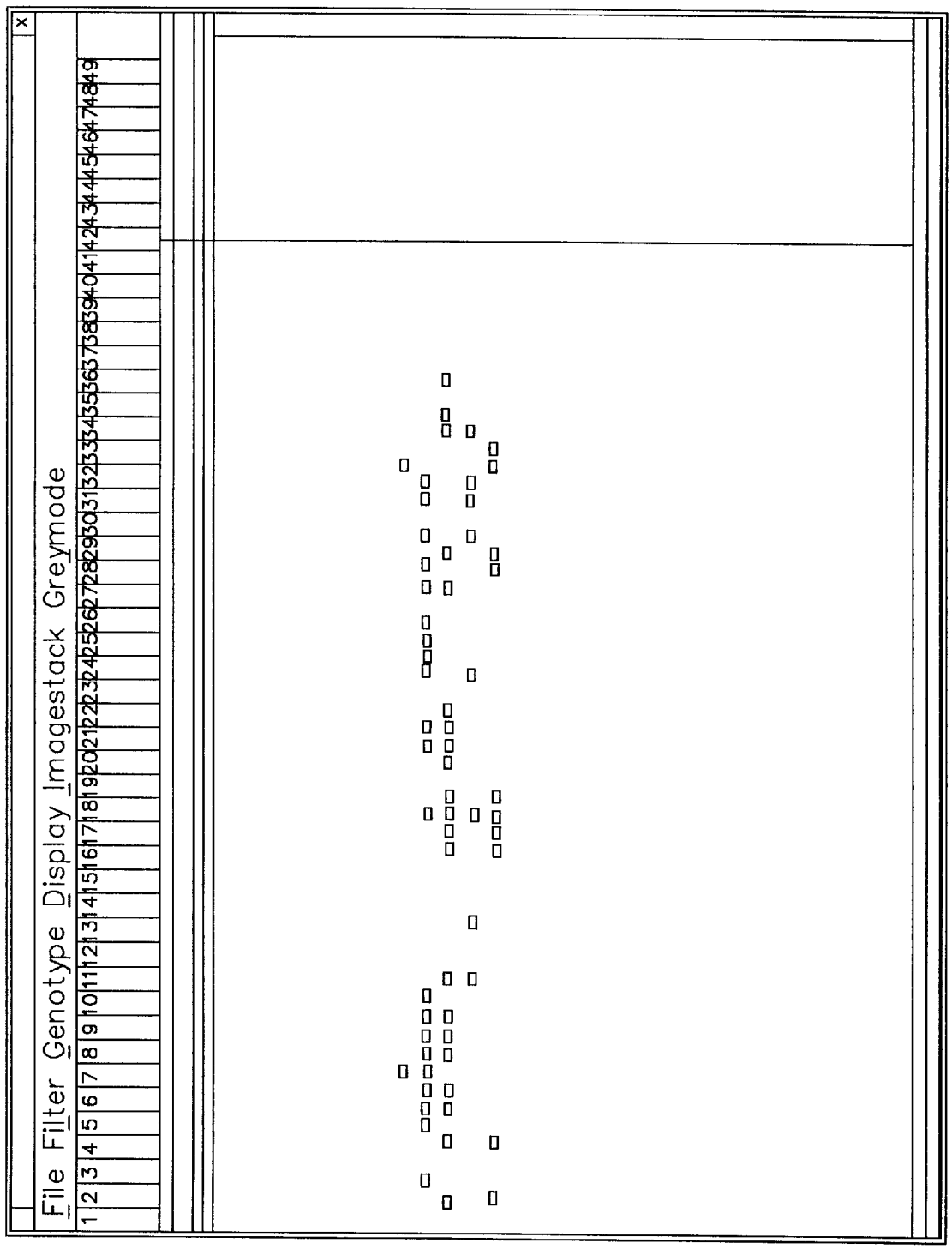
FIG. 4F is a computer screen in a gel analysis system showing the same sub-image or region of the same electrophoresis gel as in FIG. 4E, but in which channel 1 is selected to selectively display lanes containing DNA samples to be analyzed, and in which the bands have been straightened vertically and horizontally by the gel analysis system.

According to the example, after the channel 4 image of the standards has been straightened according to the above procedure, a straightened image of channel 1 may be selected to display a straightened image representing the genotypes of a number of subjects for a particular gene. FIG. 4F shows a computer screen in the gel analysis system 10, 10', or 10" (showing the same sub-image or region of the same electrophoresis gel as in FIG. 4E) but in which channel 1 is selected to selectively display lanes containing DNA samples to be analyzed, and in which the bands have been straightened vertically and horizontally by the image straightening unit, thereby enabling the gel analysis system to perform automatic analysis or autogenotyping of the gel. With reference to FIG. 4F, line 3 of display unit 53 or the computer screen (directly below the menu titles) displays the following information: the relative intensity, of the signal in a lane (lane 14); the x and y coordinates, for the position of the pointing device arrow; the lane (number) at the position of the pointing device arrow; the size, of the DNA fragment (s) corresponding to the band(s) in the lane, expressed in bp); and the call, or assignment of the band(s) in the lane to a particular allele (in this case allele no. 3).

Figure 4G:
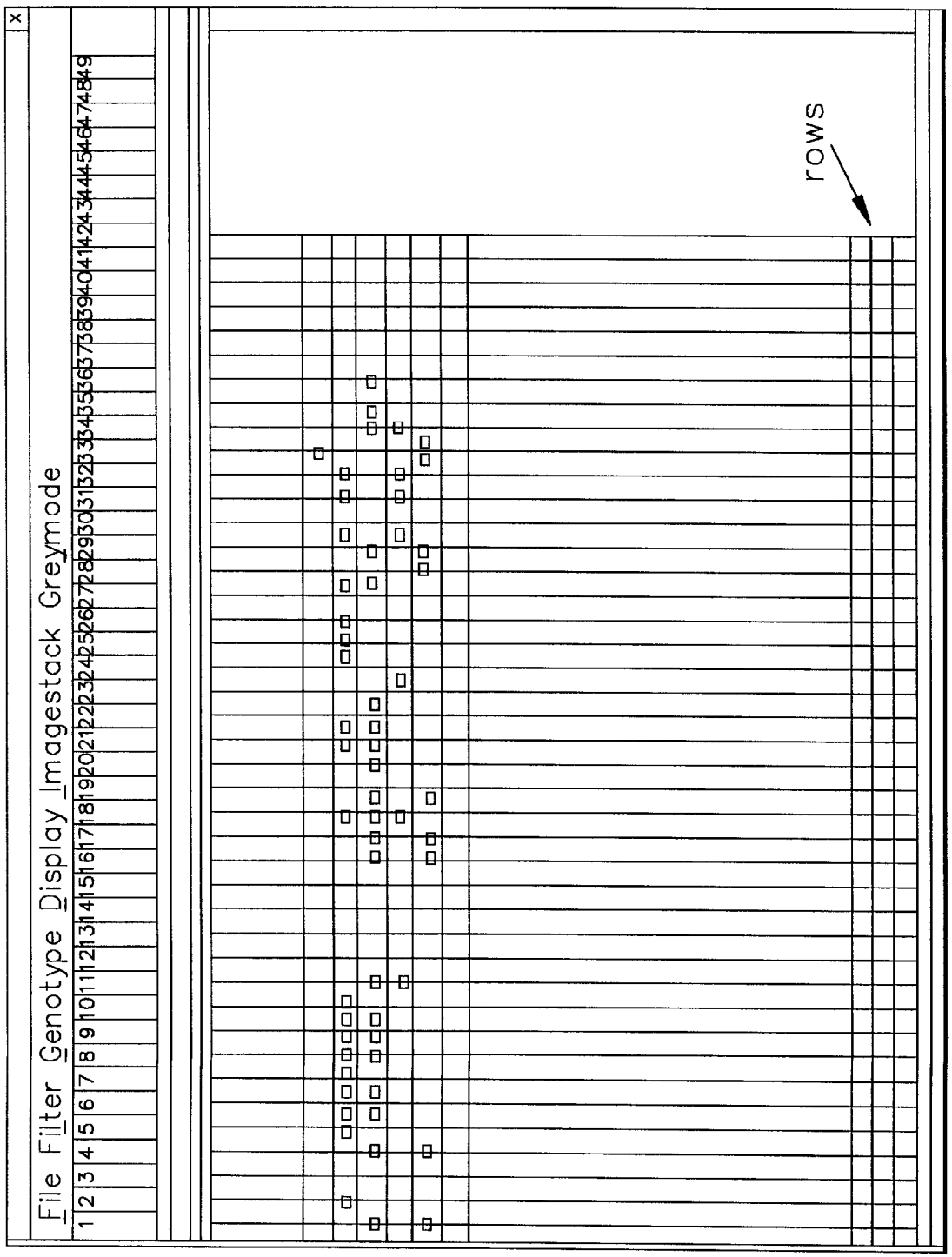
FIG. 4G is a computer screen in a gel analysis system showing an image of an electrophoresis gel in which some of the systems's available grid lines are displayed.

Viewing of the gel image may be aided by use of the grid lines unit 52. In a preferred embodiment, grid lines unit 52 may be activated by selecting "Draw Grid Lines" from the Genotype menu of the gel analysis system 10, 10', or 10", to display grid lines together with the gel image on display unit 53. The displayed grid lines can separate the bands in the horizontal (x) direction and can separate lanes in the vertical (y) direction. Vertical grid lines appear after every fourth lane, while horizontal grid lines appear with a spacing corresponding to a DNA fragment migration differential of four base pairs. The gel image may be sub-divided into a further set of grids by selecting the "Show Lanes" option from the Draw Mode menu to insert a vertical line at a location nearest the pointing device arrow which delineates adjacent lanes of the gel image. By showing a series of such vertical lines, each lane of the gel image may be delineated in this manner. FIG. 4G shows display unit 53 or a computer screen in the gel analysis system showing an image of an electrophoresis gel in which both horizontal and vertical grid lines are displayed.

The gel analysis system includes a parameter value set unit 56 for entry of parameters required for straightening the gel and for automatic genotyping of the gel (FIG. 1B). FIG. 4H shows display unit 53 or a computer screen in the gel analysis system displaying an image of an electrophoresis gel, in which the electrophoresis gel image is overlaid by a window of the gel analysis system. According to a preferred embodiment, parameter value set unit 56 involves such a window and provides for ready entry of parameters required for straightening the gel and for automatic genotyping of the gel. The numerical display from 1 to 49 along the upper part of the screen indicates lane number 14 (marked by a superimposed dark square) as the position of the pointing device arrow. The significance of the various parameters required for straightening and automatic genotyping of the gel is described hereinbelow.

Any one lane of the gel image may be selected using pointing device unit 59 by pointing to the appropriate x coordinate or horizontal position on the gel image. The lane to which a pointing device of the pointing device unit 59 is pointing is shown on a numeric lane scale displayed in the upper part of the screen, as shown in FIGS. 4A–4I. Note also that the call, or assignment of a band as corresponding to a particular allele, appears below the lane number on the numerical display across the upper part of the screen or display unit 53. Thus, with reference to FIG. 4I, for lane number 14 the call given by band call unit 47 is 3/3, indicating that the subject for lane 14 is homozygous for allele 3.

Although the call made by band call unit 47 of the gel analysis system is expressed as a numerical value corresponding to a particular allele, the absolute value for the number of base pairs of a DNA fragment in that band may be transferred to save analysis data unit 67 and the data recorded by the system. Recording of the absolute size of DNA fragments corresponding to the various bands on an analyzed gel permits comparisons to be made from gel to gel and machine to machine, etc. The ability to make comparisons of this type is particularly useful where the number of subjects to be analyzed requires the use of a plurality of gels and possibly a plurality of analysis systems or devices.

In a preferred embodiment of the invention gel analysis system 10, 10', or 10" includes an Edit Markers feature which is accessed from the File menu. The Edit Markers feature provides for a pop-down window which lists the size in bp of the DNA fragments corresponding to all the bands (alleles) in each channel. It is possible for the description of the DNA fragment sizes for a particular channel to be slightly "off", as a result the bands are not centered within the horizontal grid lines. To remedy this situation, the Edit Markers feature allows the operator to edit the marker descriptors (DNA fragment size in base pairs or bp), as necessary, to provide more accurate positioning of the grid lines delineating the bands. After editing the marker descriptors' new grid lines may be drawn in according to the procedure described above; the gel image is thereby rendered more amenable to accurate analysis by the system.

In one embodiment of the invention, automatic genotype unit 63 involves means for entering pre-defined parameters which may influence the way in which a particular gel image is analyzed. Important parameters related to gel analysis by the system include Homozygous Cut-off, Homozygous Hysteresis, and No-call Cut-off. The role and rationale for each of these parameters are described below.

The stringency with which the system calls a particular band as being homozygous or heterozygous can be determined by setting the Homozygous Cut-off parameter. In one embodiment, the Homozygous Cut-off feature is accessed via the File menu of the gel analysis system 10, 10', or 10". A typical range of values for the Homozygous Cut-off is from 0.55 to 0.75, and a more typical value would be about 0.65. By way of example, at a Homozygous Cut-off value of 0.65, if the fainter of two bands monitored by the system within a single lane has an intensity substantially less than 65% of the intensity of the stronger of the two bands, the stronger of the two bands is called or assigned as being homozygous. Or, expressed in alternative language, for a heterozygous call to be made, the fainter of the two bands must be at least 65% of the intensity of the stronger band. Thus the higher the Homozygous Cut-off value, the greater the stringency with which the system calls homozygous alleles.

The Homozygous Hysteresis parameter is coupled to, and modifies, the Homozygous Cut-off parameter by providing a bipolar range relative to the Homozygous Cut-off value, between which the system gives a "No-call" response. For example, at a Homozygous Hysteresis value of 0.05 and a Homozygous Cut-off value of 0.65, if the fainter of two bands within a lane has an intensity which is between 60% and 70% of the intensity of the stronger of the two bands, the system does not make an assignment or call.

The Homozygous Cut-off and Homozygous Hysteresis parameters are important to the system to prevent incorrect assignments as to the nature of certain bands or alleles during analysis of gel images which, though straightened, may nevertheless retain certain imperfections acquired by the gel bands during the electrophoresis and band staining processes. Such imperfections may include stutter bands, overlapping bands in homozygous alleles, and background noise on the gel, all of which are well known in the art.

Figure 4I:
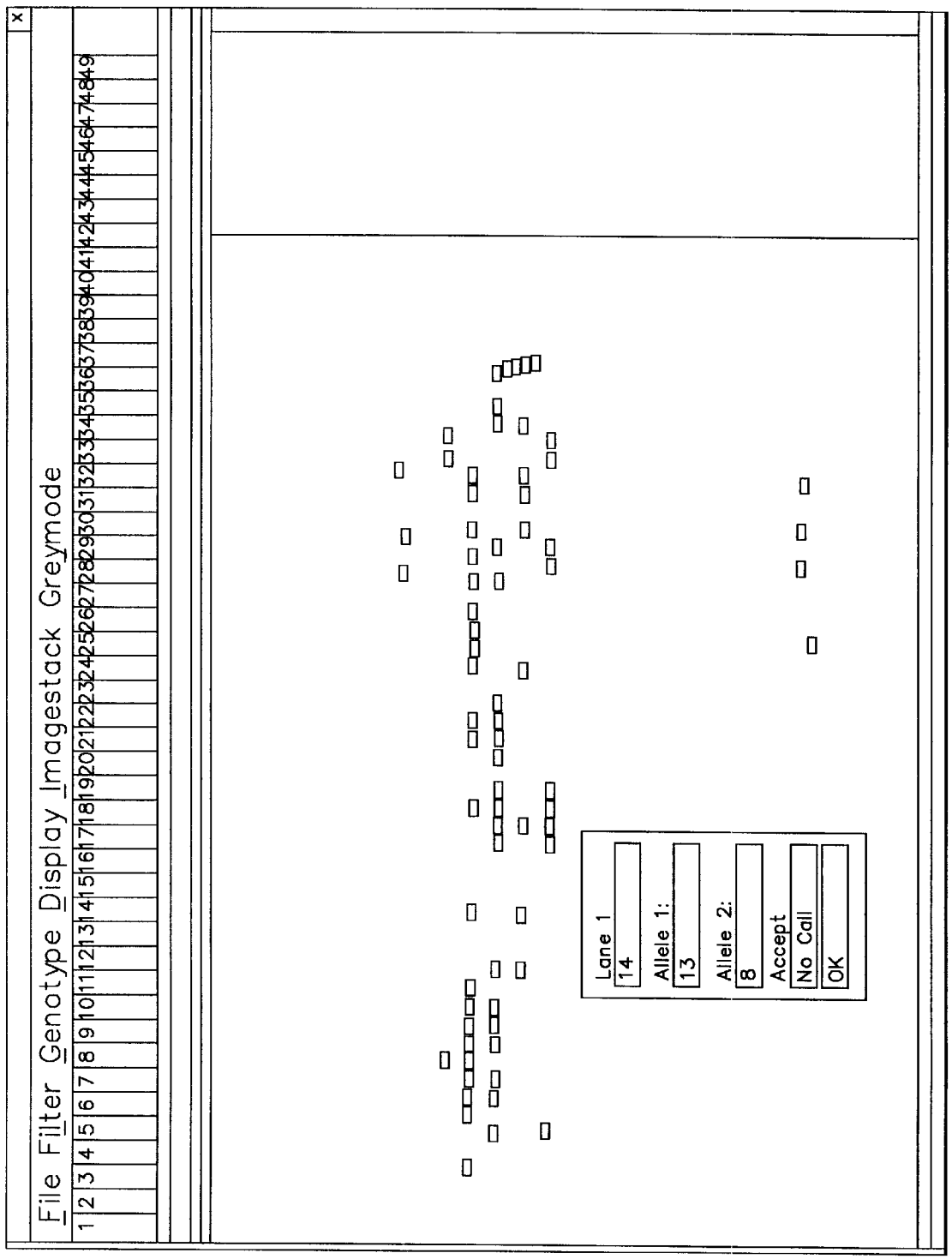
FIG. 4I is a computer screen in a gel analysis system showing a window which may be used for point-and-click intuitive editing of genotype analyses previously performed by the system in the Auto Genotype mode.

The No-Call Cut-off feature determines the minimum signal intensity, resulting from staining the gel and displaying the straightened gel image on display unit 53, that is called a (real) band by the system; below the minimum signal intensity level the system gives a "no-call" response, i.e. the region of the gel giving a sub-minimal signal intensity is considered not to be a band and is not included in the analysis. The No-Call Cut-off feature is dependent on the determination by band intensity monitoring unit 41 and band average intensity comparison unit 44 of the relative signal intensity of a given band of the gel sub-image compared with the average signal intensity of all bands of the gel sub-image. As an example, when the No-Call Cut-off parameter is set at a value of 0.85, a given band of the gel sub-image must provide a signal intensity which is at least 85% that of the average signal intensity for all bands of that gel sub-image. The higher the No-Call Cut-off parameter value the higher the stringency level and the greater the number of no-calls by the system. Regardless of the No-Call Cut-off parameter, after automatic analysis of a gel image by the system in which one or more no-calls were made, the operator may override the automatic analysis by using the edit genotype unit 65. In a preferred embodiment, edit genotype unit 65 can be activated by selecting "Edit Genotype" from the Genotype menu of the gel analysis system 10, 10', or 10". The Edit Genotype feature of gel analysis system allows the operator to go to any band of the gel image and change a no-call to a call. In addition, the Edit Genotype feature allows the operator to change the call (allele) made by band call unit 47 for a given band during automatic analysis to a different call (allele). Furthermore, the Edit Genotype feature allows the operator to change the call for a particular subject from a homozygous call to a heterozygous call. FIG. 4I shows a display unit or a computer screen in the gel analysis system showing a window which may be used for point-and-click intuitive editing of genotype analyses previously performed by automatic genotype unit 63 of the system, for example, using the Auto Genotype mode of the gel analysis system 10, 10', or 10".

Additional parameters which can be set by the operator using parameter value set unit 56', include the size (height and width) of a band to be included in the analysis, and the Allele Threshold. The maximum and minimum height and width of a standard band may be set within a pre-defined range, for example between 3 and 15 pixels in height and between 5 and 25 pixels in width. "Bands" on the image outside these ranges are considered to be background noise and are not included in the analysis. The Allele Threshold parameter is a measure of signal intensity from each pixel of the gel image. A value for the Allele Threshold parameter may be preset within the range of 0–65,000. Above the pre-set allele threshold value a pixel is counted as a real expression of signal from a band; below the allele threshold value the signal from a pixel of the image is considered to be due to background noise.

The following on-screen menus can be accessed while operating the system: File, Filter, Genotype, Display, Image Stack, and Draw Mode. Items within the File menu include:

Save Gel & Header Info, which allows a file to be saved; Open, which allows a file to be opened; Edit Markers, which allows the size of markers to be changed to a different base pair value to better accommodate the grid lines; Edit Parameters, which allows the various parameter values to be changed; Edit the Standard; and Quit. Parameters that can be changed, edited or set include: homozygous cut-off, homozygous hysteresis, no-call cut-off, maximum and minimum band image size, and allele threshold.

Items within the Filter menu include: Boost FTHR, which boosts the intensity of the bands of the gel image and at the same time gives a darker background against which to visualize the bands; and Gel Straightening, which allows the operator to perform the automatic image straightening procedure as described above.

The Genotype menu includes the following items: Manual Genotype, which allows the operator to use the computer keyboard to manually analyze any bands of a gel sub-image that, for various reasons, may not have been amenable to automatic analysis or autogenotyping; Auto Genotype, which allows the operator to instigate automatic genotyping of a gel sub-image by the gel analysis system; Edit Genotype, which allows the operator to selectively change the call assigned to any given band by the system during automatic analysis; Save Genotype, which allows for analysis information to be saved, e.g. for possible entry to a database; Draw Grid Lines, which allows for the display of grid lines over the gel image; and Locate Genotype, which allows the operator to interactively edit the analysis of a gel sub-image by clicking sequentially on each band within a given lane using the pointing device and, when candidate calls for each band appear in the pop-down window, the operator may select from the options Accept, No-Call or Cancel which appear in the window.

The Display menu includes items which allow the operator to choose either color or black and white (monochrome) display mode for output unit 30 or display unit 53.

The Image Stack menu includes items which allows the operator to go both backwards and forwards in the gel image processing and gel analysis procedures, thereby allowing a number of mutually exclusive filtering steps to be taken without the need to re-load or input the raw data for the gel image. For example, the gel image can be frozen, subsequently using filter unit 57 a filter can applied to the image, and thereafter the operator can go back to the pre-applied image.

Items included in the Draw Mode menu are as follows: Show Lanes, which draws in additional vertical grid lines which divide the gel image on a lane by lane basis (in this mode lines are drawn in at the inter-lane position closest to the pointing device arrow); Draw Black, which allows the operator to eliminate background noise which may appear on the image after image processing has occurred by selectively erasing signal from the gel image; and Draw Perfect Allele, which allows the operator to insert or replace a missing or incomplete band in a standard ladder prior to gel image straightening.

It is to be understood that analysis of a plurality of genes can be performed by the system on the same gel or gel image by selecting a different region or sub-image of the gel.

While the invention has been described primarily in the context of slab gel electrophoresis of DNA samples and genotypic analysis, the instant invention may also be used the analysis of other types of electrophoresis (for example, for various types of gels, including agarose and polyacrylamide, as well as for non-gel matrices) and for the analysis of materials other than DNA. For example, a silver-stained electrophoresis gel may also be analyzed by the system, as described below.

In the case of a silver-stained gel, only a single channel is used. Consequently, the molecular standards of known size are viewed along with, and at the same time as, the materials to be analyzed. The image of a silver-stained gel, which is displayed using output unit 30 of the gel analysis system, may be straightened by manually finding each band or row in each lane or column containing the standards. In response to a dialog box, the operator sequentially points and clicks, using for example a mouse embodiment of pointing device unit 59, on each band of the standard ladder for each lane of the standard ladder, proceeding in a horizontal direction from left to right and beginning with the lowest band (smallest molecular size) of each lane. In one embodiment of the invention, a relatively small red "X" appears on display unit 53, e.g a computer screen, at the location of each point-and-click cycle to act as a visual check for the operator that all bands of the standard have been monitored. Once all of the standards have been found and monitored the system may then straighten the gel image, by relocating all of the pixels of the image based on the series of coordinates of the standard bands, in a manner analogous to that described above for automatic straightening of a multi-dye gel image. Once the image of a silver-stained gel is straightened, it can be analyzed automatically in the edit mode of the gel analysis system.

Systems 10, 10' and 10" are general systems capable of analyzing raw data corresponding to any type of gel images. Systems 10, 10', and 10" can accept thin/horizontal, thick/vertical, fluorescent, and silver-based gel formats among others. Input data need only be a stream of integers representing pixel intensities of digitized image of an electrophoresis gel. The system is capable of analyzing gels with an arbitrary number of markers, and an arbitrary number of dyes. In order to provide these capabilities the straightening process discussed above must be robust and versatile. This is accomplished by use of gel-type header files which contains a variety of variables including gel variables describing gel attributes. The header file will be described below with reference to FIGS. 6A and 6B, but first, details of the straightening process will be discussed with reference to FIGS. 5A–5C.

Figure 5A:
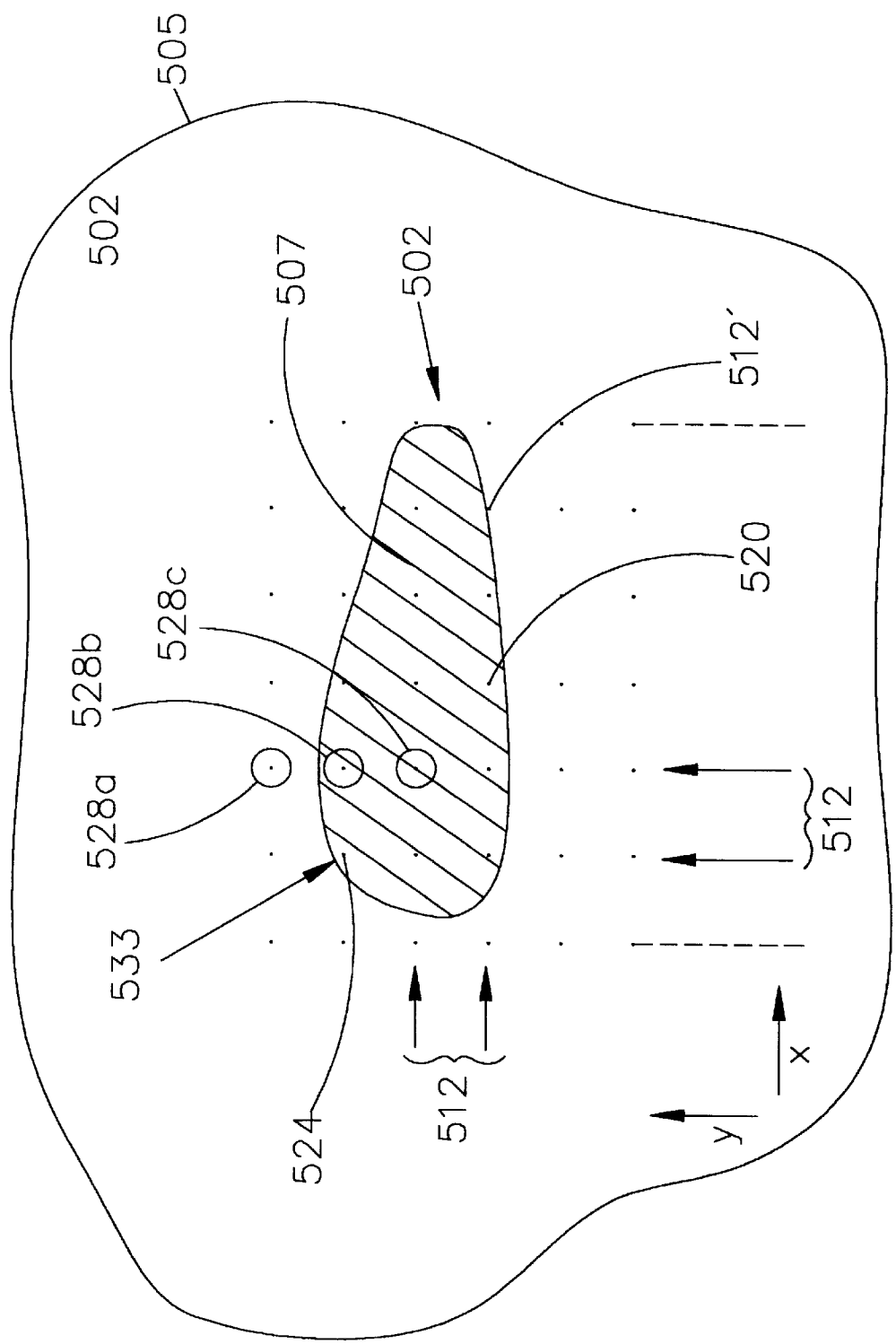
FIG. 5A shows a close-up of a typical, non-uniform, single allele on a portion of a total display.

FIG. 5A shows a close-up of a standard band 502, located at the bottom left of a gel image or sub-image. Band 502 appears as a typical, non-uniform, single band on a portion of a total display (not shown) which will be referred to as subscreen 505. Band 502 has an interior portion 507 (shaded) of varying intensity levels covering multiple pixels 512. The spacing of pixels 512 has been selected for illustrative purposes only. Interior pixels 512' are those pixels 512 interior to band 502 or within interior portion 507.

Figure 5B:
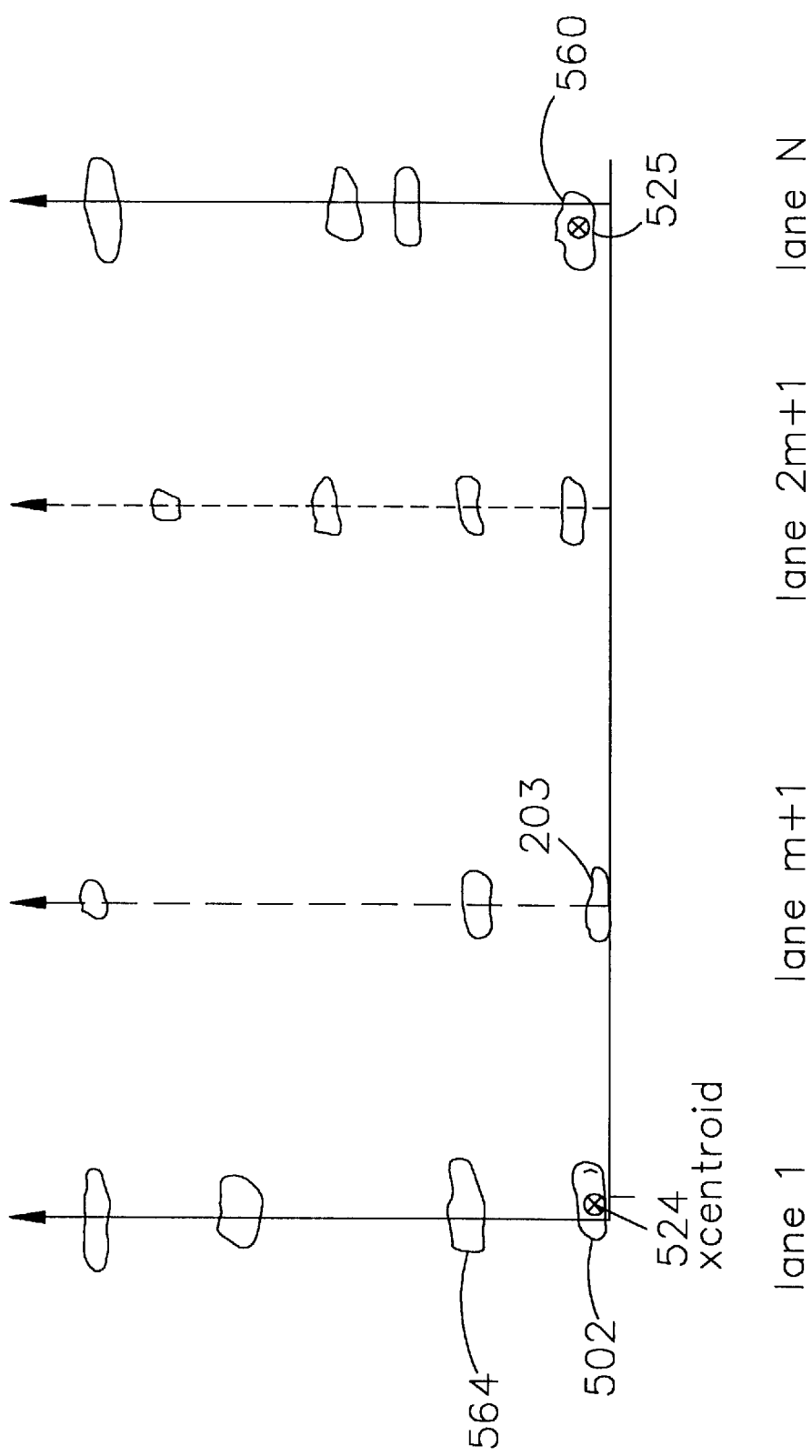
FIG. 5B shows a larger view of the screen with the left and right lanes of the gel image.
Figure 5C:
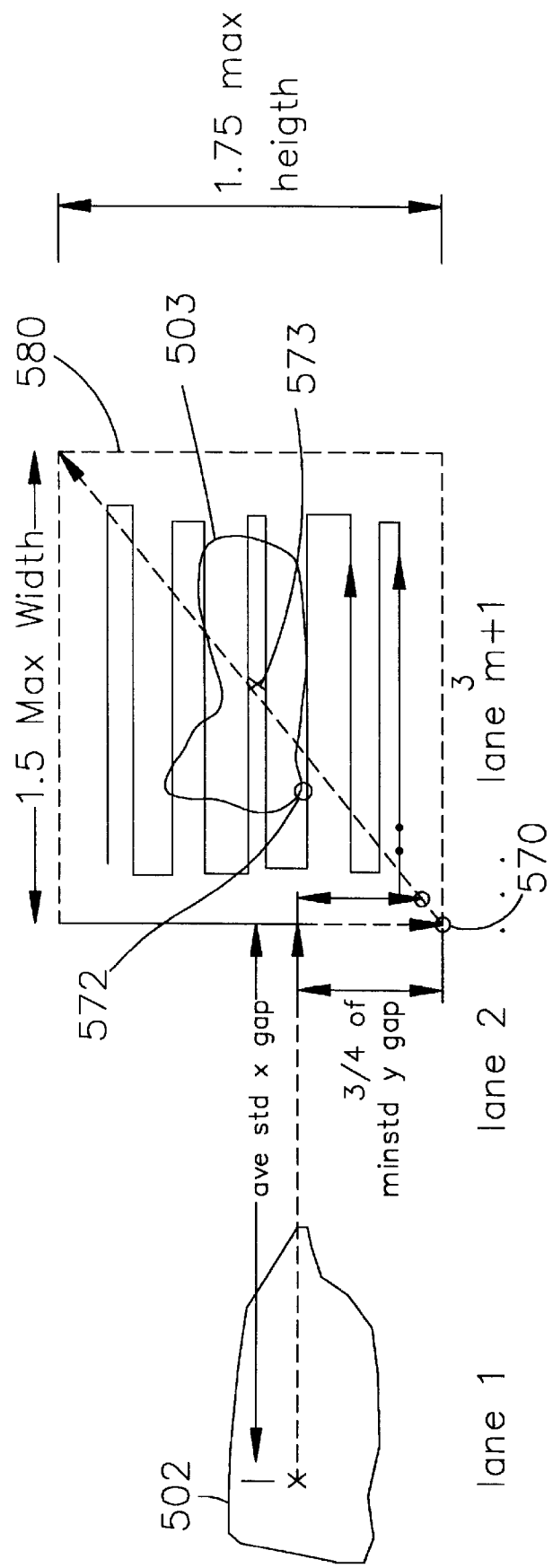
FIG. 5C shows the allele from FIG. 5B and how to proceed to locate alleles in different lanes with respect to a first allele.

Referring to FIGS. 5A–5C, when a user clicks on band 502 by visually directing pointing device 59 (such as a mouse) to interior portion 507, the interior pixel on which the user clicks (say 520) is selected. Gel analysis system 10, 10' or 10" and in particular, image straightening unit 40, 40', 40" thereof performs a check of a pixel adjacent to pixel 520 to determine whether it is still an interior pixel 512' or whether the adjacent pixel is exterior to band 502. The adjacent to be checked pixel is alternately selected to be to the left one pixel, then up or above one pixel. This process is continued until the system has recognized the top left pixel of band 502 (indicated here as pixel 524). Once the top left pixel 524 is identified, three pixels 528*a*, 528*b* and 528*c* to the right of pixel 524 are checked to determine whether they are interior pixels or exterior pixels. If top pixel 528a is exterior to band 502 and middle and bottom pixels 528b and 528c are interior, it is determined that pixel 528b is on the contour, border or edge 533 of band 502. This process is repeated to the right with pixel 528b as was done with pixel 524, until all pixels on border 533 have been identified. Once border 533 has been identified, straightening unit 40, 40' or 40" can determine the coordinates of the center or centroid of the band 502, which in this example might be pixel 524 marked by the "X" in FIG. 5B. Also, the width and height of band 502 are determined. The above process is repeated when a user clicks on the bottom right allele band 560 as will be discussed with respect to FIG. 5B.

FIG. 5B shows a larger view of the screen with the left and right lanes of the gel image. A user clicks on band 560 (lane N) and the straightening unit determines its centroid 525 and width and height as above. Image straightening unit 40, 40', 40" then proceeds upward from band 502 to identify the next band (band 564) above it. To do this, it begins at centroid 524 and moves up a parameter representing the full maximum band height, that is, the largest expected height of an band in the gel. This parameter is provided in the header file discussed below. Image straightening unit 40, 40', 40" proceeds to identify the rest of the bands in lane 1 moving up as indicated in the figure. Again, the process is repeated for lane N. Throughout this time, image straightening unit 40, 40', 40" can maintain a running average of the height and widths of the bands, and accordingly, a running average of the expected y gap or distance between bands is generated.

Since the bands in lane 1 and lane N are identified (by centroids), the image straightening unit 40, 40', 40" goes back to centroid 524 and proceeds to determine the approximate location of the next lane to the right with a standard in it (indicated by lane m+1 in FIG. 5B). To do this, image straightening unit 40, 40', 40" again uses information in the header file relating to the maximum expected height and width of the bands and the running average of the width and heights of all of the bands identified thus far as will be discussed with respect to FIG. 5C.

FIG. 5C shows band 502 from FIG. 5B, referring to both figures, image straightening unit 40, 40', 40" begins at the centroid (x,y) location of band 502 and moves to the right the average standard x gap and down ¾ of the minimum standard y gap to end up at pixel 570. Pixels are tested either scanning as shown from left to right and back left, diagonally or any other type of scan such as concentric circles. This process is continued until an interior pixel is found such as pixel 572. Straightening unit 40, 40', 40" then performs the above contour and centroid determining functions to yield centroid 573 for band 503. The searching/testing ceases if no such interior pixel is found within area 580 which covers a distance of about 1.75 times the maximum expected height of a band and 1.5 times the maximum expected width of a band. It should be noted that these distances have yielded the best results, it should be understood that a certain amount of deviation from these values might produce reasonable results. The above is repeated using centroid 573 as the starting point and the location (centroid) of the next band to the right (in lane 2m+1) is determined.

The above is repeated until the bands along the bottom row of the image have been located. Then, straightening unit 40, 40', 40" proceeds up lane m+1 (y coordinate) to determine the locations of the bands in that lane as was done and discussed with respect to lanes 1 and N. This is repeated for the rest of the standard lanes. Finally, once all of the centroids of the standard bands have been located (there may be some that do not get detected), the locations of the centroids are compared to the ideal locations (e.g. step 108 in FIG. 3A) and relocation factors are calculated (step 110, FIG. 3A), and pixels or data (including non-standard data) are relocated to their ideal location.

Raw data or a gel image file and its respective header file can be stored one per directory. The user supplies information regarding the number of dye channels, markers, and marker base-pair sizes in a header file that can be customized to fit a wide variety of genotyping (and band or allele calling) needs. The header file information can also be provided/augmented interactively by the user after the initial header file is implemented.

In one embodiment of the invention, the gel image file is called gel image and the header file that describes a number of parameters about the gel is stored in a file called gel-.header. The directory can be named anything, but in one embodiment, the directory name can indicate the date, machine, and sequence number for that machine for that date.

FIG. 6A shows an example of a gel-type header file with values (parameters or attributes) assigned numbers to the gel variables (or attributes). This example corresponds to a gel run with a standard in channel 4, a marker with 3 alleles in channel 1, and nothing of interest in channels 2 and 3. The standard has 3 rows and 16 columns spread across 61 lanes (one standard lane every four lanes). The 3 rows of the standard have allele sizes of 139, 150, and 160 base pairs, respectively. The variables or attributes are described below.

NSCANLINES states the number of scan lines gathered by the gel scanning hardware and contained in the image file.

SCANLENGTH states the number of scan lines gathered by the gel scanning hardware and contained in the image file.

STARTSCANLINE states the first scan line in the image file that is actually to be read in and analyzed by the system.

ENDSCANLINE states the last scan line in the image file that is actually to be read in and analyzed by the system.

NUMCHANNELS states the number of input sample space channels. Note: Even if only two dyes are used in the input gel, this number must be equal to the number of actual hardware sampling channels that recorded values in the gel image files.

SCANERRORLINES states that number of scan errors there were in the gel scan, and also lists the scan line numbers that are bad. This image distortion comes from the fact that the scanner gathers data on the right and left-going passes of the laser/scanner producing the image file.

FIXUPOFFSET states the small integer constant that is used to align alternate scanlines from the gel scanning hardware. This image distortion comes from the fact that the scanner gathers data on the right and left-going passes of the laser/scanner.

NSTDROWS describes the number of standard rows in the standard ladder appearing in the gel.

NSTDCOLS describes the number of standard columns in the standard ladder appearing in the gel.

NLNSBTWSTDLNS describes the number of non-standard lanes between each pair of lanes containing standard in the gel.

STDCHANNEL identifies the dye channel number (after dye separation) containing the standard ladder (1→NUMCHANNELS).

STDSIZEi is a sequence of lines, each with a separate label, describing the size (in base pairs) of each of the allele bands appearing in the standard ladder.

MAXPIXELVALUE is an integer that represents that largest possible pixel intensity that might appear in the input gel.

ALLELETHRESH is a tuned parameter that states the pixel intensity that best distinguishes a true part of an allele band from a bit of noise in the background of the image.

ALLELE_MAXHT, ALLELE_MAXWD, ALLELE_NINHT, ALLELE_MINWD are provided to describe the minimum and maximum possible band allele sizes (in pixels). They are critical in order to allow the lane straightening to be able to identify the standard bands.

NUMLANES is a parameter that states the number of lanes in the gel marker area of interest. Note that the first and last of these lanes must contain a standard lane. Also, any markers of interest to be called must be completely enclosed within the boundaries of the standard bands.

CHiTHRESHOLD is specified for each channel as the threshold of detection for the presence of significant allele information. A value above that level in the separated (but not yet boosted) dye image will then be multiplied by the BOOST factor given for that channel. In the preferred embodiment, this value is set low enough to allow amplification of significant information, but not so low as to amplify background noise.

CHIBOOST is specified for each channel as the factor to multiply against each pixel found to be above the THRESHOLD for this channel. The idea is to provide a multiplier that will boost significant information-bearing pixels above the universal ALLELETHRESH value. These values could all be set to 1.0 if the dye separation works ideally. This is a non-linear chopping back to improve badly separated gels, and may disappear in future versions.

INIT_CHANNEL is the number of the channel to be initially displayed by system 10, 10' or 10".

CHANNELMAP is a bit map of the active channels in the gel file. That is, beginning with the lowest bit in the binary representation of this number, each bit represents the presence (1) or absence (0) of that dye in the gel input file.

STRAIGHTENED is a single bit that indicates whether the gel image to be input has already been straightened/normalized or not. If the bit is 1, then the gel image has been straightened/normalized, and if it is 0, then the gel image remains unstraightened.

DYESEPMATRIX (Quickflag) is a square matrix of real values (numbers) that are used to separate the hardware input channels into the dye channels that distinguish one marker from another. The matrix is of the same dimension (both rows and columns) as the number of hardware channels. Even if the number of dyes used is less than the number of hardware channels, the matrix must be square and of the same dimension as the number of hardware sample channels written to the input image file. Quickflag, if 1, indicates that the incoming gel is not to be separated. Usually, this means that the gel was already separated and this is a file that is being input a second time. If 1, the input will be much faster, and even if the gel has not been separated, this could be useful for gathering dye separation/calibration information. The values stored in this matrix represent the normalized inverse of the coefficients of a system of equations used to describe the relation of the dye fluorescence to the reflected intensities present in each of the channels. Hence, this matrix is an inverted, normalized, dye separation matrix which automatically applies the separation matrix to the input gel image. This dye separation matrix can be modified by a user to customize it for his or her type of gel being analyzed.

ALLELES_IN_CHi the number of possible alleles for the marker in channel i is provided.

HOMOZYGOUS_CUTOFF is a fractional (between 0 and 1) value that represents what fraction of the stronger allele, the weaker allele must be in order to be identified as a heterozygous call. Nominally, if the weaker allele is less than this fraction of the larger one, then a homozygous call is made.

HOMOZYGOUS_HYSTERESIS is a value that serves as a window of uncertainty about the previous (CUTOFF) fraction. This value is also a fraction. When multiplied by the previous value, a +/− factor is formed regarding the strength of an allele band in order to be called heterozygous. For example, if the CUTOFF is 0.6 and the HYSTERESIS factor is 0.1, then if the weaker band appears to be less than 0.54 of the stronger band, the call is homozygous. If the weaker band is more than 0.66 of the stronger one, then the call is made heterozygous, if the weaker band is between 0.54 and 0.66 of the stronger one, the system will mark this as too uncertain, and will not make a call.

NO_CALL_CUTOFF is a threshold value (0, 0, . . . , 1, 0) that indicates the fraction of allele strength that a lane must have in order to be judged to contain a callable genotype. It is a fraction of the average lane strength rated across the entire gel. Note: in a hazy gel (one with a lot of background noise) this value or parameter needs to be relatively high, and in a very sharp, high-contrast gel, this value or parameter needs to be relatively small.

SIZEi are labels for lines, the labels are followed by a number representing the base pair size of one allele of the marker to be called. There are as many of these lines as the number provided on the ALLELES_IN_CHi line.

FIG. 6B shows how groups of variables or parameters are categorized within the header file. In particular, parameters 508 describe the standard. Parameters 540 correspond to the image enhancement filters. Parameters 549 correspond to the separation matrix DYESEPMATRIX, discussed above. Parameters 569 provide information for genotyping.

Numerous and additional modifications and variations of the present invention are possible in light of the above teachings. It is therefore to be understood that within the scope of the appended claims, the invention may be practiced otherwise than as specifically claimed.

What is claimed is:

1. An electrophoresis gel analysis system, including:
   a display unit configured to display a gel image of an electrophoresis gel;
   an input unit, functionally coupled to said display unit, configured to receive raw data, said raw data corresponding to an unstraightened gel image of said electrophoresis gel, said unstraightened gel image of said electrophoresis gel having a plurality of standard bands;
   a straightening unit, functionally coupled to the display unit, configured to straighten said unstraightened gel image of said electrophoresis gel and to provide a straightened gel image of said electrophoresis gel, said straightening unit comprising:
   a standards locating unit configured to locate the centers of at least two of said plurality of standard bands of said unstraightened gel image of said electrophoresis gel;
   a coordinate defining unit, coupled to said standards locating unit, configured to define x and y coordinates of the centers of said at least two of said plurality of standard bands of said unstraightened gel image of said electrophoresis gel;
   a search unit, coupled to said coordinate defining unit, configured to search said unstraightened gel image of said electrophoresis gel and to determine x and y coordinates of the centers of each of said plurality of standard bands of said unstraightened gel image of said electrophoresis gel;

a coordinate comparison unit, coupled to both said search unit and to said coordinate defining unit, configured to compare the x and y coordinates of the centers of each of said plurality of standard bands of said unstraightened gel image of said electrophoresis gel with ideal x and y coordinates of the centers of each of said plurality of standard bands of said unstraightened gel image of said electrophoresis gel;

a relocation factor calculation unit, coupled to said coordinate comparison unit, configured to calculate relocation factors for said unstraightened gel image of said electrophoresis gel; and a relocation unit, coupled to the relocation factor calculation unit, configured to relocate each pixel of each of said plurality of standard bands of said unstraightened gel image of said electrophoresis gel to its respective ideal location to provide said straightened gel image of said electrophoresis gel; and an analyzing unit coupled to said display unit, configured to analyze said straightened gel image of said electrophoresis gel wherein the analyzing unit compares an intensity of each band in the gel image to an average intensity of a plurality of bands in the gel image.

2. An electrophoresis analysis system, according to claim 1, wherein said input unit comprises:

a data receiving unit configured to receive said raw data corresponding to said unstraightened gel image of said electrophoresis gel;

a data storage unit coupled to said data receiving unit;

a data processing unit coupled to both said data receiving unit and said data storage unit; and a data transfer unit coupled to both said data processing unit and said data storage unit and configured to transfer said raw data corresponding to said unstraightened gel image of said electrophoresis gel out of said input unit.

3. The electrophoresis analysis system according to claim 1, wherein said analyzing unit comprises:

a band intensity monitoring unit configured to monitor an intensity of each band on a gel sub-image;

a band image size monitoring unit configured to monitor a size of each band on the gel sub-image;

an intra-lane band intensity comparison unit configured to compare an intensity of a first band in a lane of the gel sub-image with an intensity of a second band within the same lane of the gel sub-image;

a band average intensity comparison unit configured to compare an intensity of each band of the gel sub-image with an average intensity of all bands in the gel sub-image;

a band coordinate monitoring unit, configured to monitor coordinates of each band in the gel image;

a band image size comparison unit configured to compare the size of each band in the gel sub-image with a pre-defined band image size parameter value;

an analysis calculation unit, coupled to and receiving data input from said band image size monitoring unit, said band intensity monitoring unit, said intra-lane band intensity comparison unit, said band average intensity comparison unit, said band coordinate monitoring unit, and said band image size comparison unit and configured to provide calculated data as to the quality of each band on the gel image;

a band call unit configured to assign a value to each band on the gel image, the value representing a size of a fragment corresponding to the band; and a data download unit configured to transfer analyzed data to an external device.

4. An electrophoresis analysis system, comprising:

a display unit configured to display a gel image of an electrophoresis gel;

an input unit functionally coupled to said display unit configured to receive raw data, said raw data corresponding to an unstraightened gel image of said electrophoresis gel;

a straightening unit functionally coupled to said display unit and configured to straighten said unstraightened gel image of said electrophoresis gel to provide a straightened gel image of said electrophoresis gel; and an analyzing unit coupled to said display unit configured to analyze said straightened gel image of said electrophoresis gel, wherein the analyzing unit compares intensities of bands of the gel image to an average intensity of plural bands of the gel image.

5. The electrophoresis analysis system according to claim 4, wherein said analyzing unit is further coupled to said straightening unit.

6. The electrophoresis analysis system according to claim 4, wherein said analyzing unit comprises:

an intra-lane band intensity comparison unit configured to compare an intensity of a first band in a lane of a gel sub-image with an intensity of a second band within the same lane of the gel sub-image;

a band average intensity comparison unit configured to compare intensities of each band of the gel sub-image with an average intensity of all bands in the gel sub-image; and a band call unit configured to assign a value to each band on the gel, wherein the value represents a size of a fragment corresponding to the band.

7. The electrophoresis analysis system according to claim 4, wherein said input unit comprises:

a data receiving unit configured to receive said raw data corresponding to said unstraightened gel image of said electrophoresis gel;

a data storage unit coupled to said data receiving unit;

a data processing unit coupled to both said data receiving unit and said data storage unit; and a data transfer unit coupled to both said data processing unit and said data storage unit and configured to transfer said raw data corresponding to said unstraightened gel image of said electrophoresis gel out of said input unit.

8. An electrophoresis analysis system, comprising:

an input unit configured to receive raw data corresponding to an unstraightened gel image of an electrophoresis gel;

a straightening unit functionally coupled to said input unit and configured to straighten said unstraightened gel image of said electrophoresis gel; and an analyzing unit coupled to said straightening unit, wherein the analyzing unit compares an intensity of a first band in a lane of the gel image to an average intensity of a plurality of bands of the gel image.

9. The electrophoresis analysis system of claim 8, further comprising an output unit coupled to each of said input unit, said straightening unit, and said analyzing unit.

10. The electrophoresis analysis system of claim 9, wherein said output unit comprises a CRT or liquid crystal display.

11. The electrophoresis analysis system of claim 8, further comprising a band call unit configured to assign a value to each band in the gel image, wherein the value corresponds to a size of a fragment corresponding to the band.

12. The electrophoresis analysis system of claim 8, further comprising a band size comparison unit configured to compare a size of each band of the gel image to a pre-determined band size.

13. The electrophoresis analysis system of claim 8, further comprising a user input device, wherein a user can utilize the user input device to identify standard bands.

14. The electrophoresis analysis system of claim 8, further comprising a channel select unit, wherein the channel select unit is configured to select between different sets of bands of the gel image so that the analysis unit can operate on each set of bands individually.

15. The electrophoresis analysis system of claim 14, wherein the channel select unit includes a filter unit for filtering light emissions of bands of the gel image.

16. The electrophoresis analysis system of claim 15, wherein the filter unit can selectively pass light emissions of bands that have been dyed with a dye agent.

17. The electrophoresis analysis system of claim 8, further comprising a user input device configured to allow a user to input analysis parameters.

18. The electrophoresis analysis system of claim 17, wherein the user input device is configured to allow a user to input at least one of a homozygous cut-off parameter, a homozygous hysteresis parameter and a no-call cut-off parameter.

19. A method for displaying a straightened image of an electrophoresis gel having a plurality of standard bands on an output unit of a gel analysis system, comprising the steps of:
    inputting raw data from the electrophoresis gel to a data receiving unit of the gel analysis system;
    processing the inputted raw data to provide processed raw data;
    transferring the processed raw data to the output unit;
    displaying the processed raw data as an unstraightened image of an electrophoresis gel;
    selecting at least one standard band of the unstraightened gel image with a user input device;
    straightening the unstraightened image of the electrophoresis gel in the vertical and horizontal directions by comparing a position of the at least one selected standard band to an ideal position of the at least one selected standard band and relocating all bands in the unstraightened gel image to provide a straightened image of the electrophoresis gel; and
    displaying the straightened image of the electrophoresis gel.

20. The method of claim 19, further comprising the step of, after said step of displaying the processed raw data as an unstraightened image of the electrophoresis gel, editing the unstraightened image of the electrophoresis gel.

21. The method of claim 20, wherein said step of editing the unstraightened image of the electrophoresis gel comprises adding bands to the gel image with a user input device.

22. The method of claim 19, wherein said selecting step comprises selecting first and second standard bands of the unstraightened gel image with the user input device; and wherein the straightening step of further comprises the steps of:
    defining x and y coordinates of the centers of the first and second standard bands on the unstraightened image of the electrophoresis gel.

23. The method of claim 22, wherein the straightening step further comprises:
    locating and defining the x and y coordinates of the centers of each of the standard bands on the unstraightened image of the electrophoresis gel based on the coordinates of the first and second standard bands;
    comparing coordinates of the centers of each of the standard bands on the unstraightened image of the electrophoresis gel with ideal coordinates of the centers of the standard bands; and
    relocating each pixel of the unstraightened image of the electrophoresis gel to a new location, based on results of the comparing step, to create a straightened image.

24. A method for straightening an image of an electrophoresis gel comprising a plurality of standard bands, comprising the steps of:
    selecting a first dye channel of an output unit, the first dye channel corresponding to standard bands of the image of the electrophoresis gel;
    displaying an unstraightened image of the electrophoresis gel showing a plurality of the standard bands of the image of the electrophoresis gel;
    locating centers of at least two of the plurality of standard bands of the image of the electrophoresis gel with a user input device;
    defining x and y coordinates of the centers of the at least two of the plurality of standard bands of the image of the electrophoresis gel;
    searching the image of the electrophoresis gel to locate centers of the remaining standard bands of the image of the electrophoresis gel;
    defining x and y coordinates of the centers of the remaining standard bands of the image of the electrophoresis gel;
    comparing the coordinates of the centers of each of the plurality of standard bands of the image of the electrophoresis gel with ideal coordinates of the centers of each of the plurality of standard bands;
    calculating relocation factors; and
    creating a straightened image of the electrophoresis gel utilizing the relocation factors.

25. A method for analyzing an image of an electrophoresis gel, comprising the steps of:
    determining an intensity of each band of the image of the electrophoresis gel;
    calculating an average intensity for all bands of the image of the electrophoresis gel;
    comparing the intensity of each band with the calculated average intensity to determine whether each band meets a pre-defined intensity parameter;
    determining locations of each band on the image of the electrophoresis gel; and
    assigning a numerical value to bands of the image of the electrophoresis gel based on the intensity and location of the band, wherein the value represents a size of a fragment corresponding to the band.

26. The method of claim 25, wherein in the assigning step, no value is assigned to bands that fail to meet the pre-defined intensity parameter in the comparing step.

27. The method of claim 25, further comprising the step of comparing an intensity of a first band in a lane of the gel image with an intensity of a second band in the same lane of the gel image.

28. A method for analyzing an image of an electrophoresis matrix, comprising the steps:

receiving raw image data of the electrophoresis matrix;

displaying an unstraightened image of the electrophoresis matrix based on the received raw data;

straightening the unstraightened image of the electrophoresis matrix to provide a straightened image of the electrophoresis matrix;

comparing an intensity of a first band in a lane of the straightened image to an intensity of a second band in the same lane;

determining locations of bands of the straightened image; and analyzing the straightened image based on results of the comparison step and determined locations of the bands to assign values to the bands that represent sizes of fragments corresponding to the bands.

29. The method of claim 27, wherein in the assigning step, no value is assigned to a band if the band has an intensity that is below a predetermined percentage of an intensity of another band in the same lane of the gel image.

30. The method of claim 28, wherein said analyzing step comprises one of automatically analyzing the image of the electrophoresis gel and manually analyzing the image of the electrophoresis gel.

31. The method of claim 28, wherein in the analyzing step, no value is assigned to a band if an intensity of the band is less than a predetermined percentage of an intensity of another band in the same lane of the straightened image.

32. A method of straightening an unstraightened gel image, comprising the steps of:

a) operating a user input device to point to a pixel of a first standard band of the unstraightened gel image, and determining x and y coordinates for a centroid of the first standard band;

b) determining x and y coordinates for centroids of additional standard bands of the unstraightened gel image;

c) comparing the x and y coordinates for the determined centroids with ideal x and y coordinates for the centroids; and d) generating a straightened gel image based on results of the comparing step.

33. The method of claim 32, wherein said step a) comprises the steps of:

by means of a pointing device, pointing to a first pixel of the first standard band of the unstraightened gel image;

successively checking an intensity of a plurality of pixels adjacent the first pixel to determine whether each of the plurality of pixels is inside the first standard band, wherein the plurality of pixels are progressively more distant from the first pixel; and determining a contour of the first standard band of the unstraightened gel image.

34. The method of claim 32, wherein step b) comprises searching for a pixel of a second standard band adjacent the first standard band by successively checking an intensity of pixels adjacent the first standard band according to a pre-determined pattern.

35. The method of claim 34, wherein the searching step comprises checking an intensity of pixels adjacent the first standard band that are located a predetermined distance from the centroid of the first standard band, and wherein the predetermined distance is based on an expected size of the standard bands of the unstraightened gel image.

* * * * *